(12) United States Patent
McEachern et al.

(10) Patent No.: US 10,913,733 B2
(45) Date of Patent: Feb. 9, 2021

(54) SUBSTITUTED PIPERIDINES THIAZOLYL ACETAMIDES AS GLYCOSIDASE INHIBITORS AND USES THEREOF

(71) Applicant: Merck Sharp & Dohme Corp., Rahway, NJ (US)

(72) Inventors: Ernest J. McEachern, Burnaby (CA); Harold G. Selnick, Ambler, PA (US); Yuanxi Zhou, Richmond (CA)

(73) Assignees: Alectos Therapeutics Inc., Burnaby (CA); Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/061,988

(22) PCT Filed: Dec. 14, 2016

(86) PCT No.: PCT/US2016/066507
§ 371 (c)(1),
(2) Date: Jun. 13, 2018

(87) PCT Pub. No.: WO2017/106254
PCT Pub. Date: Jun. 22, 2017

(65) Prior Publication Data
US 2018/0362517 A1  Dec. 20, 2018

Related U.S. Application Data

(60) Provisional application No. 62/269,243, filed on Dec. 18, 2015.

(51) Int. Cl.
*A61K 31/454* (2006.01)
*C07D 417/06* (2006.01)
*C07D 417/14* (2006.01)
*C07D 409/06* (2006.01)

(52) U.S. Cl.
CPC ......... *C07D 417/06* (2013.01); *C07D 409/06* (2013.01); *C07D 417/14* (2013.01)

(58) Field of Classification Search
CPC .............................. A61K 31/454; C07D 417/06
USPC .......................................... 514/326; 546/209
See application file for complete search history.

(56) References Cited

U.S. PATENT DOCUMENTS

| | | | |
|---|---|---|---|
| 5,935,974 A | 8/1999 | Rae et al. | |
| 8,008,326 B2 | 8/2011 | Borza et al. | |
| 9,879,001 B2 | 1/2018 | Yu et al. | |
| 2008/0300276 A1 | 12/2008 | Borza et al. | |
| 2011/0053982 A1 | 3/2011 | Fay et al. | |
| 2011/0060012 A1 | 3/2011 | Meyers et al. | |

FOREIGN PATENT DOCUMENTS

WO    WO 17/106254    *  6/2017

OTHER PUBLICATIONS

Jordan, V. C. Nature Reviews: Drug Discovery, 2, 2003, 205.*
Hackam, et al. JAMA, 296(14), 2006, 1731-1732.*
Written Opinion for WO2107/106254, PCT/US16/66507 (dated Mar. 10, 2017).

* cited by examiner

*Primary Examiner* — Douglas M Willis
(74) *Attorney, Agent, or Firm* — J. Eric Thies; John C. Todaro

(57) ABSTRACT

The present invention is directed to thiazolyl piperidine compounds of the general structural formula I:

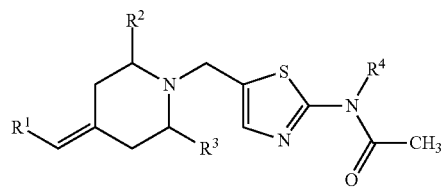

which are inhibitors of O-GlcNAcase. The present invention is also directed to uses of the compounds described herein in the potential treatment or prevention of neurological and psychiatric disorders and diseases in which O-GlcNAcase is involved. The present invention is also directed to compositions comprising these compounds. The present invention is also directed to uses of these compositions in the potential prevention or treatment of such diseases in which O-GlcNAcase is involved.

21 Claims, No Drawings

SUBSTITUTED PIPERIDINES THIAZOLYL ACETAMIDES AS GLYCOSIDASE INHIBITORS AND USES THEREOF

CROSS REFERENCE TO RELATED APPLICATIONS

This application is a U.S. National Phase application under 35 U.S.C. § 371 of PCT Application No. PCT/US2016/066507, filed Dec. 14, 2016, which claims priority from US Provisional Application No. U.S. 62/269,243, filed Dec. 18, 2015.

BACKGROUND OF THE INVENTION

A wide range of cellular proteins, both nuclear and cytoplasmic, are post-translationally modified by the addition of the monosaccharide 2-acetamido-2-deoxy-β-D-glucopyranoside (β-N-acetylglucosamine) which is attached via an O-glycosidic linkage. This modification is generally referred to as O-linked N-acetylglucosamine or O-GlcNAc. The enzyme responsible for post-translationally linking 3-N-acetylglucosamine (GlcNAc) to specific serine and threonine residues of numerous nucleocytoplasmic proteins is O-GlcNAc transferase (OGT). A second enzyme, known as glycoprotein 2-acetamido-2-deoxy-β-D-glucopyranosidase (O-GlcNAcase) removes this post-translational modification to liberate proteins making the O-GlcNAc-modification a dynamic cycle occurring several times during the lifetime of a protein.

O-GlcNAc-modified proteins regulate a wide range of vital cellular functions including, for example, transcription, proteasomal degradation, and cellular signaling. O-GlcNAc is also found on many structural proteins. For example, it has been found on a number of cytoskeletal proteins, including neurofilament proteins, synapsins, synapsin-specific clathrin assembly protein AP-3, and ankyrinG. O-GlcNAc modification has been found to be abundant in the brain. It has also been found on proteins clearly implicated in the etiology of several diseases including Alzheimer's disease (AD) and cancer.

For example, it is well established that AD and a number of related tauopathies including Downs' syndrome, Pick's disease, Niemann-Pick Type C disease, and amyotrophic lateral sclerosis (ALS) are characterized, in part, by the development of neurofibrillary tangles (NFTs). These NFTs are aggregates of paired helical filaments (PHFs) and are composed of an abnormal form of the cytoskeletal protein "tau". Normally tau stabilizes a key cellular network of microtubules that is essential for distributing proteins and nutrients within neurons. In AD patients, however, tau becomes hyperphosphorylated, disrupting its normal functions, forming PHFs and ultimately aggregating to form NFTs. Six isoforms of tau are found in the human brain. In AD patients, all six isoforms of tau are found in NFTs, and all are markedly hyperphosphorylated. Tau in healthy brain tissue bears only 2 or 3 phosphate groups, whereas those found in the brains of AD patients bear, on average, 8 phosphate groups. A clear parallel between NFT levels in the brains of AD patients and the severity of dementia strongly supports a key role for tau dysfunction in AD. The precise causes of this hyperphosphorylation of tau remain elusive. Accordingly, considerable effort has been dedicated toward: a) elucidating the molecular physiological basis of tau hyperphosphorylation; and b) identifying strategies that could limit tau hyperphosphorylation in the hope that these might halt, or even reverse, the progression of Alzheimer's disease. Thus far, several lines of evidence suggest that up-regulation of a number of kinases may be involved in hyperphosphorylation of tau, although an alternative basis for this hyperphosphorylation has been advanced.

In particular, it has emerged that phosphate levels of tau are regulated by the levels of O-GlcNAc on tau. The presence of O-GlcNAc on tau has stimulated studies that correlate O-GlcNAc levels with tau phosphorylation levels. The interest in this field stems from the observation that O-GlcNAc modification has been found to occur on many proteins at amino acid residues that are also known to be phosphorylated. Consistent with this observation, it has been found that increases in phosphorylation levels result in decreased O-GlcNAc levels and conversely, increased O-GlcNAc levels correlate with decreased phosphorylation levels. This reciprocal relationship between O-GlcNAc and phosphorylation has been termed the "Yin-Yang hypothesis" and has gained strong biochemical support by the discovery that the enzyme OGT forms a functional complex with phosphatases that act to remove phosphate groups from proteins. Like phosphorylation, O-GlcNAc is a dynamic modification that can be removed and reinstalled several times during the lifespan of a protein. Suggestively, the gene encoding O-GlcNAcase has been mapped to a chromosomal locus that is linked to AD. Hyperphosphorylated tau in human AD brains has markedly lower levels of O-GlcNAc than are found in healthy human brains. It has been shown that O-GlcNAc levels of soluble tau protein from human brains affected with AD are markedly lower than those from healthy brain. Furthermore, PHF from diseased brain was suggested to lack completely any O-GlcNAc modification whatsoever. The molecular basis of this hypoglycosylation of tau is not known, although it may stem from increased activity of kinases and/or dysfunction of one of the enzymes involved in processing O-GlcNAc. Supporting this latter view, in both PC-12 neuronal cells and in brain tissue sections from mice, a nonselective N-acetylglucosamindase inhibitor was used to increase tau O-GlcNAc levels, whereupon it was observed that phosphorylation levels decreased. The implication of these collective results is that by maintaining healthy O-GlcNAc levels in AD patients, such as by inhibiting the action of O-GlcNAcase, one should be able to block hyperphosphorylation of tau and all of the associated effects of tau hyperphosphorylation, including the formation of NFTs and downstream effects. However, because the proper functioning of the β-hexosaminidases is critical, any potential therapeutic intervention for the treatment of AD that blocks the action of O-GlcNAcase would have to avoid the concomitant inhibition of both hexosaminidases A and B.

Neurons do not store glucose and therefore the brain relies on glucose supplied by blood to maintain its essential metabolic functions. Notably, it has been shown that within brain, glucose uptake and metabolism decreases with aging. Within the brains of AD patients marked decreases in glucose utilization occur and are thought to be a potential cause of neurodegeneration. The basis for this decreased glucose supply in AD brain is thought to stem from any of decreased glucose transport, impaired insulin signaling, and decreased blood flow.

In light of this impaired glucose metabolism, it is worth noting that of all glucose entering into cells, 2-5% is shunted into the hexosamine biosynthetic pathway, thereby regulating cellular concentrations of the end product of this pathway, uridine diphosphate-N-acetylglucosamine (UDP-GlcNAc). UDP-GlcNAc is a substrate of the nucleocytoplasmic enzyme O-GlcNAc transferase (OGT), which acts to post-translationally add GlcNAc to specific serine and threonine residues of numerous nucleocytoplasmic proteins. OGT recognizes many of its substrates and binding partners through its tetratricopeptide repeat (TPR) domains. As described above, O-GlcNAcase removes this post-translational modification to liberate proteins making the O-GlcNAc-modification a dynamic cycle occurring several times during the lifetime of a protein. O-GlcNAc has been found in several proteins on known phosphorylation sites, including tau and neurofilaments. Additionally, OGT shows unusual kinetic behaviour making it exquisitely sensitive to intracellular UDP-GlcNAc substrate concentrations and therefore glucose supply. Consistent with the known properties of the hexosamine biosynthetic pathway, the enzymatic properties of OGT, and the reciprocal relationship between O-GlcNAc and phosphorylation, it has been shown that decreased glucose availability in brain leads to tau hyperphosphorylation. Therefore the gradual impairment of glucose transport and metabolism, whatever its causes, leads to decreased O-GlcNAc and hyperphosphorylation of tau (and other proteins). Accordingly, the inhibition of O-GlcNAcase should compensate for the age related impairment of glucose metabolism within the brains of healthy individuals as well as patients suffering from AD or related neurodegenerative diseases.

These results suggest that a malfunction in the mechanisms regulating tau O-GlcNAc levels may be vitally important in the formation of NFTs and associated neurodegeneration. Good support for blocking tau hyperphosphorylation as a therapeutically useful intervention comes from recent studies showing that when transgenic mice harbouring human tau are treated with kinase inhibitors, they do not develop typical motor defects and, in another case, show decreased levels of insoluble tau. These studies provide a clear link between lowering tau phosphorylation levels and alleviating AD-like behavioural symptoms in a murine model of this disease. Indeed, pharmacological modulation of tau hyperphosphorylation is widely recognized as a potential therapeutic strategy for treating AD and other neurodegenerative disorders.

Small-molecule O-GlcNAcase inhibitors, to limit tau hyperphosphorylation, have been considered for treatment of AD and related tauopathies. Specifically, the O-GlcNAcase inhibitor thiamet-G has been implicated in the reduction of tau phosphorylation in cultured PC-12 cells at pathologically relevant sites. Moreover, oral administration of thiamet-G to healthy Sprague-Dawley rats has been implicated in reduced phosphorylation of tau at Thr231, Ser396 and Ser422 in both rat cortex and hippocampus.

There is also a large body of evidence indicating that increased levels of O-GlcNAc protein modification provides protection against pathogenic effects of stress in cardiac tissue, including stress caused by ischemia, hemorrhage, hypervolemic shock, and calcium paradox. For example, activation of the hexosamine biosynthetic pathway (HBP) by administration of glucosamine has been demonstrated to exert a protective effect in animal models of ischemia/reperfusion, trauma hemorrhage, hypervolemic shock, and calcium paradox. Moreover, strong evidence indicates that these cardioprotective effects are mediated by elevated levels of protein O-GlcNAc modification. There is also evidence that the O-GlcNAc modification plays a role in a variety of neurodegenerative diseases, including Parkinson's disease and Huntington's disease.

Humans have three genes encoding enzymes that cleave terminal β-N-acetyl-glucosamine residues from glycoconjugates. The first of these encodes O-GlcNAcase. O-GlcNAcase is a member of family 84 of glycoside hydrolases that includes enzymes from organisms as diverse as prokaryotic pathogens to humans. O-GlcNAcase acts to hydrolyse O-GlcNAc off of serine and threonine residues of post-translationally modified proteins. Consistent with the presence of O-GlcNAc on many intracellular proteins, the enzyme O-GlcNAcase appears to have a role in the etiology of several diseases including type II diabetes, Alzheimer's disease, and cancer. Although O-GlcNAcase was likely isolated earlier on, about 20 years elapsed before its biochemical role in acting to cleave O-GlcNAc from serine and threonine residues of proteins was understood. More recently O-GlcNAcase has been cloned, partially characterized, and suggested to have additional activity as a histone acetyltransferase. However, little was known about the catalytic mechanism of this enzyme. The other two genes, HEXA and HEXB, encode enzymes catalyzing the hydrolytic cleavage of terminal β-N-acetylglucosamine residues from glycoconjugates. The gene products of HEXA and HEXB predominantly yield two dimeric isozymes, hexosaminidase A and hexosaminidase B, respectively. Hexosaminidase A ($\alpha\beta$), a heterodimeric isozyme, is composed of an $\alpha$- and ß-subunit. Hexosaminidase B ($\beta\beta$), a homodimeric isozyme, is composed of two β-subunits. The two subunits, $\alpha$- and ß-, bear a high level of sequence identity. Both of these enzymes are classified as members of family 20 of glycoside hydrolases and are normally localized within lysosomes. The proper functioning of these lysosomal β-hexosaminidases is critical for human development, a fact that is underscored by the genetic illnesses, Tay-Sach's and Sandhoff diseases which stem from a dysfunction in, respectively, hexosaminidase A and hexosaminidase B. These enzymatic deficiencies cause an accumulation of glycolipids and glycoconjugates in the lysosomes resulting in neurological impairment and deformation. The deleterious effects of accumulation of gangliosides at the organismal level are still being uncovered.

As a result of the biological importance of these β-N-acetyl-glucosaminidases, small molecule inhibitors of glycosidases have received a great deal of attention, both as tools for elucidating the role of these enzymes in biological processes and in developing potential therapeutic applications. The control of glycosidase function using small molecules offers several advantages over genetic knockout studies including the ability to rapidly vary doses or to entirely withdraw treatment. However, a major challenge in developing inhibitors for blocking the function of mammalian glycosidases, including O-GlcNAcase, is the large number of functionally related enzymes present in tissues of higher eukaryotes. Accordingly, the use of non-selective inhibitors in studying the cellular and organismal physiological role of one particular enzyme is complicated because complex phenotypes arise from the concomitant inhibition of such functionally related enzymes. In the case of β-N-acetylglucosaminidases, many compounds that act to block O-GlcNAcase function are non-specific and act potently to inhibit the lysosomal β-hexosaminidases. Accordingly, there is a need in the art for compounds that inhibit O-GlcNAcase function.

SUMMARY OF THE INVENTION

The present invention is directed to thiazolyl piperidine compounds which are inhibitors of O-GlcNAcase. The present invention is also directed to uses of the compounds described herein in the potential treatment or prevention of neurological and psychiatric disorders and diseases in which O-GlcNAcase is involved. The present invention is also directed to compositions comprising these compounds. The present invention is also directed to uses of these compositions in the potential prevention or treatment of such diseases in which O-GlcNAcase is involved.

DETAILED DESCRIPTION OF THE INVENTION

The present invention is directed to compounds of the formula I:

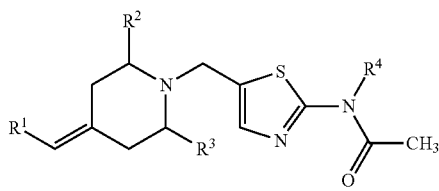

wherein:

R¹ is selected from the group consisting of:
phenyl, pyridyl, benzodioxolyl, dihydrobenzodioxinyl, indolyl, oxoisoindolinyl, pyrazolyl, and pyrimidinyl, which is substituted with one or more $R^{1a}$, $R^{1b}$ and $R^{1c}$, wherein $R^{1a}$, $R^{1b}$ and $R^{1c}$ are independently selected from the group consisting of:
(a) hydrogen,
(b) hydroxy,
(c) halogen,
(d) $C_{1-6}$alkyl, which is unsubstituted or substituted with substituents selected from the group consisting of: hydroxy, 1-3 fluoro, —OCH₃, —OCH₂CH₂OCH₃, —(C═O)—$C_{1-6}$alkyl, —NH₂, —NH($C_{1-6}$alkyl), and —N($C_{1-6}$alkyl)₂, and —NH(C═O)($C_{1-6}$alkyl),
(e) —O—$C_{1-6}$alkyl, which is unsubstituted or substituted with substituents selected from the group consisting of: hydroxy, 1-3 fluoro, —OCH₃, —(C═O)—$C_{1-6}$alkyl, —NH₂, —NH($C_{1-6}$alkyl), and —N($C_{1-6}$alkyl)₂, and —NH(C═O)($C_{1-6}$alkyl),
(f) —O—$C_{3-6}$alkenyl,
(g) —NH₂,
(h) —NH($C_{1-6}$alkyl),
(i) —N($C_{1-6}$alkyl)₂,
(j) —(C═O)NH₂,
(k) —(C═O)NH($C_{1-6}$alkyl),
(l) —(C═O)N($C_{1-6}$alkyl)₂,
(m) —(C═O)—$C_{1-6}$alkyl,
(n) —(C═O)O—$C_{1-6}$alkyl,
(o) —O(C═O)O—$C_{1-6}$alkyl,
(p) -phenyl,
(q) —SO₂NH₂,
(r) —SO₂N($C_{1-6}$alkyl)₂, and
(s) —NO₂;

R² is hydrogen or methyl;
R³ is hydrogen or methyl; and
R⁴ is hydrogen or methyl;
or a pharmaceutically acceptable salt thereof.

An embodiment of the present invention includes compounds of the formula Ia:

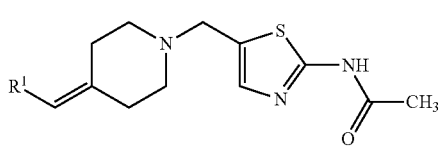

wherein R¹ is defined herein; or a pharmaceutically acceptable salt thereof.

An embodiment of the present invention includes compounds of the formula Ib:

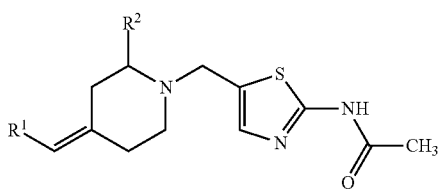

wherein R¹ and R² are defined herein; or a pharmaceutically acceptable salt thereof.

An embodiment of the present invention includes compounds of the formula Ic:

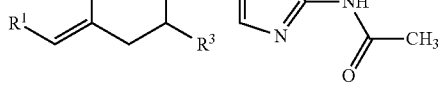

wherein R¹ and R³ are defined herein; or a pharmaceutically acceptable salt thereof.

An embodiment of the present invention includes compounds of the formula IIa:

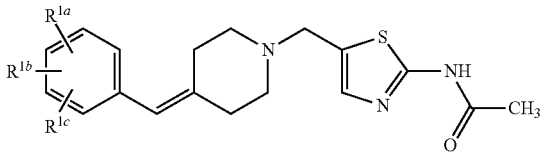

wherein $R^{1a}$, $R^{1b}$ and $R^{1c}$ are defined herein; or a pharmaceutically acceptable salt thereof.

An embodiment of the present invention includes compounds of the formula IIb:

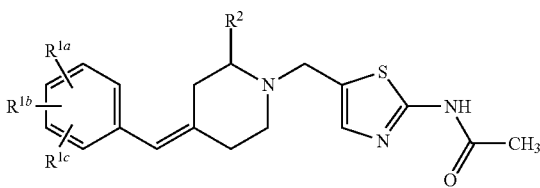

wherein $R^{1a}$, $R^{1b}$, $R^{1c}$ and $R^2$ are defined herein; or a pharmaceutically acceptable salt thereof.

An embodiment of the present invention includes compounds of the formula IIc:

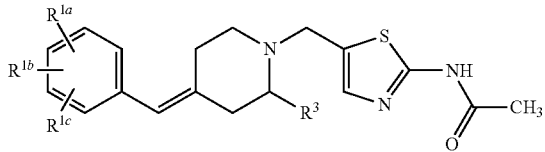

IIc wherein $R^{1a}$, $R^{1b}$, $R^{1c}$ and $R^3$ are defined herein; or a pharmaceutically acceptable salt thereof.

An embodiment of the present invention includes compounds of the formula IIIa:

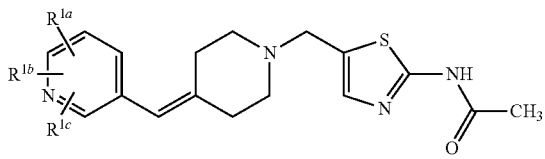

IIIa wherein $R^{1a}$, $R^{1b}$ and $R^{1c}$ are defined herein; or a pharmaceutically acceptable salt thereof.

An embodiment of the present invention includes compounds of the formula IIIb:

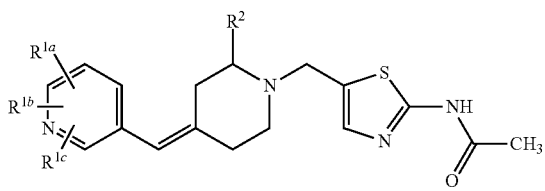

IIIb wherein $R^{1a}$, $R^{1b}$, $R^{1c}$ and $R^2$ are defined herein; or a pharmaceutically acceptable salt thereof.

An embodiment of the present invention includes compounds of the formula IIc:

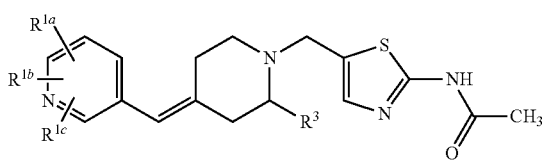

IIIc wherein $R^{1a}$, $R^{1b}$, $R^{1c}$ and $R^3$ are defined herein; or a pharmaceutically acceptable salt thereof.

An embodiment of the present invention includes compounds wherein $R^1$ is selected from the group consisting of phenyl, pyridin-3-yl, 1,3-benzodioxol-5-yl, 1,3-dihydro-1,4-benzodioxin-6-yl, 1H-indol-5-yl, 1-oxoisoindolin-5-yl, pyrazol-4-yl, and pyrimidin-5-yl, which is substituted with $R^{1a}$, $R^{1b}$ and $R^{1c}$.

An embodiment of the present invention includes compounds wherein $R^1$ is phenyl, which is substituted with $R^{1a}$, $R^{1b}$ and $R^{1c}$, or pyridyl, which is substituted with $R^{1a}$, $R^{1b}$ and $R^{1c}$.

An embodiment of the present invention includes compounds wherein $R^1$ is pyridyl, which is substituted with $R^{1a}$, $R^{1b}$ and $R^{1c}$.

An embodiment of the present invention includes compounds wherein $R^1$ is phenyl or pyridyl, which is substituted with $R^{1a}$, $R^{1b}$ and $R^{1c}$, wherein $R^{1a}$, $R^{1b}$ and $R^{1c}$ are independently selected from the group consisting of:
(a) hydrogen,
(b) hydroxyl,
(c) halogen,
(d) $C_{1-6}$alkyl, which is unsubstituted or substituted with a substituent selected from the group consisting of: hydroxy, 1-3 fluoro, and —$OCH_3$, and
(e) —O—$C_{1-6}$alkyl, which is unsubstituted or substituted with a substituent selected from the group consisting of: hydroxy, 1-3 fluoro, and —$OCH_3$.

An embodiment of the present invention includes compounds wherein $R^1$ is phenyl or pyridyl, which is substituted with $R^{1a}$, $R^{1b}$ and $R^{1c}$, wherein $R^{1a}$, $R^{1b}$ and $R^{1c}$ are independently selected from the group consisting of:
(a) hydrogen,
(b) hydroxyl,
(c) fluoro,
(d) $C_{1-3}$alkyl, which is unsubstituted or substituted with a substituent selected from the group consisting of: hydroxy, 1-3 fluoro, and —$OCH_3$,
(e) —O—$C_{1-3}$alkyl, which is unsubstituted or substituted with a substituent selected from the group consisting of: 1-3 fluoro, and —$OCH_3$.

An embodiment of the present invention includes compounds wherein $R^1$ is phenyl or pyridyl, which is substituted with $R^{1a}$, $R^{1b}$ and $R^{1c}$, wherein $R^{1c}$ is hydrogen, and $R^{1a}$ and $R^{1b}$ are independently selected from the group consisting of:
(a) hydrogen,
(b) hydroxyl,
(c) fluoro,
(d) $C_{1-3}$alkyl, which is unsubstituted or substituted with a substituent selected from the group consisting of: hydroxy, 1-3 fluoro, and —$OCH_3$,
(e) —O—$C_{1-3}$alkyl, which is unsubstituted or substituted with a substituent selected from the group consisting of: 1-3 fluoro, and —$OCH_3$.

An embodiment of the present invention includes compounds wherein $R^2$ and $R^3$ are each hydrogen. An embodiment of the present invention includes compounds wherein $R^2$ is methyl and $R^3$ is hydrogen. An embodiment of the present invention includes compounds wherein $R^2$ is hydrogen and $R^3$ is methyl. An embodiment of the present invention includes compounds wherein $R^4$ is hydrogen. An embodiment of the present invention includes compounds wherein $R^4$ is methyl.

Exemplifying the invention is the use of the compounds disclosed in the Examples and herein. Specific compounds within the present invention include a compound which is selected from the group consisting of the compounds disclosed in the following Examples and pharmaceutically acceptable salts thereof and individual enantiomers or diastereomers thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. In addition, the present invention embraces all geometric and positional isomers. For example, if a compound of the present invention contains a double bond, both the cis- and trans-forms, as well as mixtures, are embraced within the invention. The present invention is meant to comprehend all such isomeric forms of these compounds. Formula I shows the structure of the class of compounds without specific stereochemistry. At least some of the chemical names of compounds of the invention as set forth in this application may have been generated on an automated basis by use of commercially available chemical naming software programs, and have not been independently verified.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

The present invention also includes all pharmaceutically acceptable isotopic variations of a compound of formula I in which one or more atoms is replaced by atoms having the same atomic number, but an atomic mass or mass number different from the atomic mass or mass number usually found in nature. Examples of isotopes suitable for inclusion in the compounds of the invention include isotopes of hydrogen such as $^2$H and $^3$H, carbon such as $^{11}$C, $^{13}$C and $^{14}$C, nitrogen such as $^{13}$N and $^{15}$N, oxygen such as $^{15}$O, $^{17}$O and $^{18}$O, phosphorus such as $^{32}$P, sulfur such as $^{35}$S, fluorine such as $^{18}$F, iodine such as $^{123}$I and $^{125}$I, and chlorine such as $^{36}$Cl. Certain isotopically-labelled compounds of formula I, for example those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. An embodiment of the present invention includes compounds that are substituted with a positron emitting isotope. An embodiment of the present invention includes compounds that are substituted with a $^{11}$C isotope. An embodiment of the present invention includes compounds that are substituted with an $^{18}$F isotope. In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

As used herein the singular forms "a", "and", and "the" include plural referents unless the context clearly dictates otherwise. For example, "a compound" refers to one or more of such compounds, while "the enzyme" includes a particular enzyme as well as other family members and equivalents thereof as known to those skilled in the art.

Throughout this application, it is contemplated that the term "compound" or "compounds" refers to the compounds discussed herein and includes precursors and derivatives of the compounds, and pharmaceutically acceptable salts thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

"Alkyl" refers to a straight or branched hydrocarbon chain group consisting solely of carbon and hydrogen atoms, containing no unsaturation and including, for example, from one to ten carbon atoms, such as 1, 2, 3, 4, 5, 6, 7, 8, 9, or 10 carbon atoms, and which is attached to the rest of the molecule by a single bond. In alternative embodiments, the alkyl group may contain from one to eight carbon atoms, such as 1, 2, 3, 4, 5, 6, 7, or 8 carbon atoms. In alternative embodiments, the alkyl group may contain from one to six carbon atoms, such as 1, 2, 3, 4, 5, or 6 carbon atoms. In alternative embodiments, the alkyl group may contain from one to three carbon atoms, such as 1, 2, or 3 carbon atoms. Unless stated otherwise specifically in the specification, the alkyl group may be optionally substituted by one or more substituents as described herein. Unless stated otherwise specifically herein, it is understood that the substitution can occur on any carbon of the alkyl group.

"Alkenyl" refers to a straight or branched hydrocarbon chain group consisting solely of carbon and hydrogen atoms, containing at least one double bond and including, for example, from two to ten carbon atoms, such as 2, 3, 4, 5, 6, 7, 8, 9, or 10 carbon atoms, and which is attached to the rest of the molecule by a single bond or a double bond. In alternative embodiments, the alkenyl group may contain from two to eight carbon atoms, such as 2, 3, 4, 5, 6, 7, or 8 carbon atoms. In alternative embodiments, the alkenyl group may contain from three to six carbon atoms, such as 3, 4, 5, or 6 carbon atoms. In alternative embodiments, the alkenyl group may contain from one to three carbon atoms, such as 1, 2, or 3 carbon atoms. Unless stated otherwise specifically in the specification, the alkenyl group may be optionally substituted by one or more substituents as described herein. Unless stated otherwise specifically herein, it is understood that the substitution can occur on any carbon of the alkenyl group.

"Optional" or "optionally" means that the subsequently described event of circumstances may or may not occur, and that the description includes instances where said event or circumstance occurs one or more times and instances in which it does not. For example, "optionally substituted alkyl" means that the alkyl group may or may not be substituted and that the description includes both substituted alkyl groups and alkyl groups having no substitution, and that said alkyl groups may be substituted one or more times. Examples of optionally substituted alkyl groups include, without limitation, methyl, ethyl, propyl, etc.; examples of optionally substituted alkenyl groups include allyl, crotyl, 2-pentenyl, 3-hexenyl, etc. In some embodiments, optionally substituted alkyl include $C_{1-6}$ alkyls. Substituents (such as $R^{1a}$, $R^{1b}$ and $R^{1c}$) may be absent if the valency of the group to which they are attached does not permit such substitution. A group which is designated as being independently substituted with substituents may be independently substituted with multiple numbers of such substituents.

In alternative embodiments of the present invention, the compound may selectively inhibit an O-glycoprotein 2-acetamido-2-deoxy-3-D-glucopyranosidase (O-GlcNAcase); the compound may selectively bind an O-GlcNAcase (e.g., a mammalian O-GlcNAcase); the compound may selectively inhibit the cleavage of a 2-acetamido-2-deoxy-β-D-glucopyranoside (O-GlcNAc); the compound may not substantially inhibit a mammalian β-hexosaminidase. In alternative aspects, a compound of the present invention may have enhanced permeability.

In another aspect, the invention provides a pharmaceutical composition including a compound according to the invention, and pharmaceutically acceptable salts, thereof in combination with a pharmaceutically acceptable carrier.

In another aspect, the invention provides methods of selectively inhibiting an O-GlcNAcase, or of inhibiting an O-GlcNAcase in a subject in need thereof, or of increasing the level of O-GlcNAc, or of potentially treating Alzheimer's disease and related tauopathies, amyotrophic lateral sclerosis, Progressive supranuclear palsy, glaucoma, schizophrenia, Huntington's disease, Parkinson's disease, mild cognitive impairment, neuropathy and cancer or stress, in a subject in need thereof, by administering to the subject an effective amount of a compound of formula I and pharmaceutically acceptable salts thereof.

In another aspect, the invention provides a method for screening for a selective inhibitor of an O-GlcNAcase, by
a) contacting a first sample with a test compound;
b) contacting a second sample with a compound of formula I or a pharmaceutically acceptable salt thereof;
c) determining the level of inhibition of the O-GlcNAcase in the first and second samples, where the test compound is a selective inhibitor of a O-GlcNAcase if the test compound exhibits the same or greater inhibition of the O-GlcNAcase when compared to the compound of the present invention.

In alternative aspects, the invention provides methods of synthesis to prepare a compound as described herein, or a pharmaceutically acceptable salt thereof.

The invention provides, in part, novel compounds that are capable of inhibiting an O-glycoprotein 2-acetamido-2-deoxy-β-D-glucopyranosidase (O-GlcNAcase). In some embodiments, the O-GlcNAcase may be a mammalian O-GlcNAcase, such as a rat, mouse or human O-GlcNAcase.

In some embodiments, one or more of the compounds according to the invention may exhibit enhanced permeability. Permeability can be assessed using a variety of standard experimental techniques, including without limitation in situ perfusion, ex vivo tissue diffusion, in vitro cell monolayers (e.g. Caco-2 cells, MDCK cells, LLC-PK1 cells), and artificial cell membranes (e.g. PAMPA assay); suitable techniques for measuring effective permeability (Per) or apparent peameability ($P_{app}$) are reviewed for example by Volpe in *The AAPS Journal*, 2010, 12(4), 670-678. In some embodiments, one or more of the compounds according to the invention may show enhanced permeability when tested in one or more of these assays for determining Par or $P_{app}$. In some embodiments, a compound that exhibits enhanced permeability may exhibit greater oral absorption. In some embodiments, a compound that exhibits enhanced permeability may exhibit greater brain penetrance when administered in vivo. In some embodiments, a compound that exhibits enhanced permeability may achieve higher brain concentrations when administered in vivo. In some embodiments, a compound that exhibits enhanced permeability may exhibit a higher brain/plasma concentration ratio when administered in vivo. In some embodiments, "enhanced permeability" means an increase in measured $P_{eff}$ or $P_{app}$ by any value between 10% and 100%, or of any integer value between 10% and 100%, for example, 10%, 20%, 30%, 40%, 50%, 60%, 70%, 80%, 90%, 100%, or over 100%, or an increase by 1-fold, 2-fold, or 3-fold, or more, as compared to a suitable reference compound disclosed in for example WO 2006/092049 or WO 2008/025170. A suitable reference compound may be, for example, (3aR,5R,6S,7R,7aR)-5-(hydroxymethyl)-2-propyl-5,6,7,7a-tetrahydro-3 aH-pyrano[3,2-d]thiazole-6,7-diol, or (3aR,5R,6S,7R,7aR)-2-(ethylamino)-5-(hydroxymethyl)-5,6,7,7a-tetrahydro-3aH-pyrano[3,2-d]thiazole-6,7-diol, or (3aR,5R,6S,7R,7aR)-2-(dimethylamino)-5-(hydroxymethyl)-5,6,7,7a-tetrahydro-3aH-pyrano[3,2-d]thiazole-6,7-diol. In some embodiments, "enhanced permeability" means a measurable $P_{app}$ value (i.e. a value greater than zero) in the assay described below for determination of $P_{app}$ in LLC-PK1 cells. In some embodiments, "enhanced permeability" means a $P_{app}$ value greater than $2\times10^{-6}$ cm/s in the assay described below for determination of $P_{app}$ in LLC-PK1 cells. In alternative embodiments, "enhanced permeability" means a $P_{app}$ value in the range $2\times10^{-6}$ cm/s to $35\times10^{-6}$ cm/s in the assay described below for determination of $P_{app}$ in LLC-PK1 cells.

In some embodiments, a compound according to the invention may exhibit superior selectivity in inhibiting an O-GlcNAcase. In some embodiments, one or more of the compounds according to the invention may be more selective for an O-GlcNAcase over a β-hexosaminidase. In some embodiments, one or more of the compounds may selectively inhibit the activity of a mammalian O-GlcNAcase over a mammalian β-hexosaminidase. In some embodiments, a selective inhibitor of an O-GlcNAcase may not substantially inhibit a β-hexosaminidase. In some embodiments, the β-hexosaminidase may be a mammalian β-hexosaminidase, such as a rat, mouse or human β-hexosaminidase. A compound that "selectively" inhibits an O-GlcNAcase is a compound that may inhibit the activity or biological function of an O-GlcNAcase, but may not substantially inhibit the activity or biological function of a β-hexosaminidase. For example, in some embodiments, a selective inhibitor of an O-GlcNAcase may selectively inhibit the cleavage of 2-acetamido-2-deoxy-β-D-glucopyranoside (O-GlcNAc) from polypeptides. In some embodiments, a selective inhibitor of an O-GlcNAcase may selectively bind to an O-GlcNAcase. In some embodiments, a selective inhibitor of an O-GlcNAcase may inhibit hyperphosphorylation of a tau protein and/or inhibit formations of NFTs. By "inhibit," "inhibition" or "inhibiting" means a decrease by any value between 10% and 90%, or of any integer value between 30% and 60%, or over 100%, or a decrease by 1-fold, 2-fold, 5-fold, 10-fold or more. It is to be understood that the inhibiting does not require full inhibition. In some embodiments, a selective inhibitor of an O-GlcNAcase may elevate or enhance O-GlcNAc levels e.g., O-GlcNAc-modified polypeptide or protein levels, in cells, tissues, or organs (e.g., in brain, muscle, or heart (cardiac) tissue) and in animals. By "elevating" or "enhancing" is meant an increase by any value between 10% and 90%, or of any integer value between 30% and 60%, or over 100%, or an increase by 1-fold, 2-fold, 5-fold, 10-fold, 15-fold, 25-fold, 50-fold, 100-fold or more. In some embodiments, a selective inhibitor of an O-GlcNAcase may exhibit a selectivity ratio, as described herein, in the range 10 to 100000, or in the range 100 to 100000, or in the range 1000 to 100000, or at least 10, 20, 50, 100, 200, 500, 1000, 1500, 2000, 2500, 3000, 3500, 4000, 4500, 5000, 6000, 7000, 10,000, 25,000, 50,000, 75,000, or any value within or about the described range.

One or more of the compounds of the present invention may elevate O-GlcNAc levels on O-GlcNAc-modified polypeptides or proteins in vivo specifically via interaction with an O-GlcNAcase enzyme, and may be effective in treating conditions which require or respond to inhibition of O-GlcNAcase activity.

In some embodiments, one or more of the compounds of the present invention may be useful as agents that produce a decrease in tau phosphorylation and NFT formation. In some embodiments, one or more of the compounds may therefore be useful to treat Alzheimer's disease and related tauopathies. In some embodiments, one or more of the compounds may thus be capable of treating Alzheimer's disease and related tauopathies by lowering tau phosphorylation and reducing NFT formation as a result of increasing tau O-GlcNAc levels. In some embodiments, one or more of the compounds may produce an increase in levels of O-GlcNAc modification on O-GlcNAc-modified polypeptides or proteins, and may therefore be useful for treatment of disorders responsive to such increases in O-GlcNAc modification; these disorders may include, without limitation, neurodegenerative, inflammatory, cardiovascular, and immunoregulatory diseases. In some embodiments, a compound may also be useful as a result of other biological activities related to its ability to inhibit the activity of glycosidase enzymes. In alternative embodiments, one or more of the compounds of the invention may be useful for screening or identification of diseases or disorders associated with O-GlcNAcase dysfunction in a patient. In alternative embodiments, one or more of the compounds of the invention may be valuable tools in studying the physiological role of O-GlcNAc at the cellular and organismal level.

In alternative embodiments, the invention provides methods of enhancing or elevating levels of protein O-GlcNAc modification in animal subjects, such as, veterinary and human subjects. In alternative embodiments, the invention provides methods of selectively inhibiting an O-GlcNAcase enzyme in animal subjects, such as, veterinary and human subjects. In alternative embodiments, the invention provides methods of inhibiting phosphorylation of tau polypeptides, or inhibiting formation of NFTs, in animal subjects, such as, veterinary and human subjects.

The present invention provides methods of treating conditions that are modulated, directly or indirectly, by an O-GlcNAcase enzyme or by O-GlcNAc-modified protein levels, for example, a condition that is benefited by inhibition of an O-GlcNAcase enzyme or by an elevation of O-GlcNAc-modified protein levels. Such conditions may include, without limitation, glaucoma, schizophrenia, tauopathies, such as Alzheimer's disease, neurodegenerative diseases, cardiovascular diseases, diseases associated with inflammation, diseases associated with immunosuppression and cancers. One or more of the compounds of the invention may also be useful in the treatment of diseases or disorders related to deficiency or over-expression of O-GlcNAcase or accumulation or depletion of O-GlcNAc, or any disease or disorder responsive to glycosidase inhibition therapy. Such diseases and disorders may include, but are not limited to, glaucoma, schizophrenia, Huntington's disease, Parkinson's disease, Amyotrophic lateral sclerosis, mild cognitive impairment (MCI), neuropathy, neurodegenerative disorders, such as Alzheimer's disease (AD), or cancer. Such diseases and disorders may also include diseases or disorders related to the accumulation or deficiency in the enzyme OGT. Also included is a method of protecting or treating target cells expressing proteins that are modified by O-GlcNAc residues, the dysregulation of which modification may result in disease or pathology.

In alternative embodiments, the invention provides methods of enhancing or elevating levels of protein O-GlcNAc modification in animal subjects, such as, veterinary and human subjects. This elevation of O-GlcNAc levels may be useful for the prevention or treatment of Alzheimer's disease; prevention or treatment of other neurodegenerative diseases (e.g. Parkinson's disease, Huntington's disease); providing neuroprotective effects; preventing damage to cardiac tissue; and treating diseases associated with inflammation or immunosuppression.

In alternative embodiments, the invention provides methods of selectively inhibiting an O-GlcNAcase enzyme in animal subjects, such as veterinary and human subjects. In alternative embodiments, the invention provides methods of inhibiting phosphorylation of tau polypeptides, or inhibiting formation of NFTs, in animal subjects, such as, veterinary and human subjects. Accordingly, a compound of the invention may be used to study and treat AD and other tauopathies.

In general, the methods of the invention may be effected by administering a compound according to the invention to a subject in need thereof, or by contacting a cell or a sample with a compound according to the invention, for example, a pharmaceutical composition comprising a therapeutically effective amount of the compound of formula I. More particularly, they may be useful in the treatment of a disorder in which the regulation of O-GlcNAc protein modification is implicated, or any condition as described herein. Disease states of interest may include Alzheimer's disease (AD) and related neurodegenerative tauopathies, in which abnormal hyperphosphorylation of the microtubule-associated protein tau is involved in disease pathogenesis. In some embodiments, a compound may be used to block hyperphosphorylation of tau by maintaining elevated levels of O-GlcNAc on tau, thereby providing therapeutic benefit.

The effectiveness of a compound in treating pathology associated with the accumulation of toxic tau species (for example, Alzheimer's disease and other tauopathies) may be confirmed by testing the ability of a compound to block the formation of toxic tau species in established cellular and/or transgenic animal models of disease.

Tauopathies that may be treated with a compound of the invention may include, without limitation: Alzheimer's disease, Amyotrophic lateral sclerosis with cognitive impairment (ALSci), Argyrophilic grain dementia, Bluit disease, Corticobasal degeneration (CBD), Dementia pugilistica, Diffuse neurofibrillary tangles with calcification, Down's syndrome, Familial British dementia, Familial Danish dementia, Frontotemporal dementia with parkinsonism linked to chromosome 17 (FTDP-17), Gerstmann-Straussler-Scheinker disease, Guadeloupean parkinsonism, Hallevorden-Spatz disease (neurodegeneration with brain iron accumulation type 1), Multiple system atrophy, Myotonic dystrophy, Niemann-Pick disease (type C), Pallido-ponto-nigral degeneration, Parkinsonism-dementia complex of Guam, Pick's disease (PiD), Post-encephalitic parkinsonism (PEP), Prion diseases (including Creutzfeldt-Jakob Disease (CJD), Variant Creutzfeldt-Jakob Disease (vCJD), Fatal Familial Insomnia, and Kuru), Progressive supercortical gliosis, Progressive supranuclear palsy (PSP), Richardson's syndrome, Subacute sclerosing panencephalitis, Tangle-only dementia, and Glaucoma.

One or more of the compounds of this invention may also be useful in the treatment of conditions associate with tissue damage or stress, stimulating cells, or promoting differentiation of cells. Accordingly, in some embodiments, a compound of this invention may be used to provide therapeutic benefit in a variety of conditions or medical procedures involving stress in cardiac tissue; such conditions may include, without limitation: ischemia; hemorrhage; hypovolemic shock; myocardial infarction; an interventional cardiology procedure; cardiac bypass surgery; fibrinolytic therapy; angioplasty; and stent placement.

The effectiveness of a compound in treating pathology associated with cellular stress (including ischemia, hemorrhage, hypovolemic shock, myocardial infarction, and other cardiovascular disorders) may be confirmed by testing the ability of a compound to prevent cellular damage in established cellular stress assays, and to prevent tissue damage and promote functional recovery in animal models of ischemia-reperfusion, and trauma-hemorrhage.

Compounds that selectively inhibit O-GlcNAcase activity may be used for the treatment of diseases that are associated with inflammation; such conditions may include, without limitation: inflammatory or allergic diseases such as asthma, allergic rhinitis, hypersensitivity lung diseases, hypersensitivity pneumonitis, eosinophilic pneumonias, delayed-type hypersensitivity, atherosclerosis, interstitial lung disease (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies, insect sting allergies; autoimmune diseases, such as rheumatoid arthritis, psoriatic arthritis, multiple sclerosis, Guillain-Barré syndrome, systemic lupus erythematosus, myastenia gravis, glomerulonephritis, autoimmune thyroiditis, graft rejection, including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as dermatitis, eczema, atopic dermatitis, allergic contact dermatitis, urticaria; vasculitis (e.g., necrotizing, cutaneous, and hypersensitivity vasculitis); eosinphilic myotis, eosiniphilic fasciitis; and cancers.

In addition, compounds that affect levels of protein O-GlcNAc modification may be used for the treatment of diseases associated with immunosuppression, such as, for example, in individuals undergoing chemotherapy, radiation therapy, enhanced wound healing and burn treatment, therapy for autoimmune disease or other drug therapy (e.g., corticosteroid therapy) or combination of conventional drugs used in the treatment of autoimmune diseases and graft/transplantation rejection, which causes immunosuppression; or immunosuppression due to congenital deficiency in receptor function or other causes.

One or more of the compounds of the invention may be useful for treatment of neurodegenerative diseases; such conditions may include, without limitation, Parkinson's disease and Huntington's disease. Other conditions that may be treated are those triggered, affected, or in any other way correlated with levels of O-GlcNAc post-translational protein modification. It is expected that one or more of the compounds of this invention may be useful for the treatment of such conditions and in particular, but not limited to, the following for which a association with O-GlcNAc levels on proteins has been established: graft rejection, in particular but not limited to solid organ transplants, such as heart, lung, liver, kidney, and pancreas transplants (e.g. kidney and lung allografts); cancer, in particular but not limited to cancer of the breast, lung, prostate, pancreas, colon, rectum, bladder, kidney, ovary; as well as non-Hodgkin's lymphoma and melanoma; epilepsy, pain, fibromyalgia, or stroke, e.g., for neuroprotection following a stroke.

Pharmaceutical compositions including compounds according to the invention, or for use according to the invention, are contemplated as being within the scope of the invention. In some embodiments, pharmaceutical compositions including an effective amount of a compound of the present invention or a pharmaceutically acceptable salt thereof in combination with a pharmaceutically acceptable carrier (as defined below) are provided.

The compounds of present invention or a pharmaceutically acceptable salts thereof may be useful because they may have pharmacological activity in animals, including humans. In some embodiments, one or more of the compounds according to the invention may be stable in plasma, when administered to a subject.

In some embodiments, a compound according to the invention, or for use according to the invention, may be provided in combination with any other active agents or pharmaceutical compositions where such combined therapy may be useful to modulate O-GlcNAcase activity, for example, to treat neurodegenerative, inflammatory, cardiovascular, or immunoregulatory diseases, or any condition described herein. In some embodiments, a compound according to the invention, or for use according to the invention, may be provided in combination with one or more agents useful in the prevention or treatment of Alzheimer's disease. Examples of such agents may include, without limitation, acetylcholine esterase inhibitors (AChEIs) such as Aricept® (Donepezil), Exelon® (Rivastigmine), Razadyne® (Razadyne ER®, Reminyl®, Nivalin®, Galantamine), Cognex® (Tacrine), Dimebon, Huperzine A, Phenserine, Debio-9902 SR (ZT-1 SR), Zanapezil (TAK0147), ganstigmine, NP7557, etc.;

NMDA receptor antagonists such as Namenda® (Axura®, Akatinol®, Ebixa®, Memantine), Dimebon, SGS-742, Neramexane, Debio-9902 SR (ZT-1 SR), etc.;

gamma-secretase inhibitors and/or modulators such as Flurizan™ (Tarenflurbil, MPC-7869, R-flurbiprofen), LY450139, MK 0752, E2101, BMS-289948, BMS-299897, BMS-433796, LY-411575, GSI-136, etc.;

beta-secretase inhibitors such as ATG-Z1, CTS-21166, verubecestat, etc.;

alpha-secretase activators, such as NGX267, etc;

amyloid-β aggregation and/or fibrillization inhibitors such as Alzhemed™ (3APS, Tramiprosate, 3-amino-1-propanesulfonic acid), AL-108, AL-208, AZD-103, PBT2, Cereact, ONO-2506PO, PPI-558, etc.;

tau aggregation inhibitors such as methylene blue, etc.;

microtubule stabilizers such as AL-108, AL-208, paclitaxel, etc.;

RAGE inhibitors, such as TTP488, etc.;

5-HT1a receptor antagonists, such as Xaliproden, Lecozotan, etc.;

5-HT4 receptor antagonists, such as PRX-03410, etc.;

kinase inhibitors such as SRN-003-556, amfurindamide, LiC, AZD1080, NPO31112, SAR-502250, etc.

humanized monoclonal anti-Aβ antibodies such as Bapineuzumab (AAB-001), LY2062430, RN1219, ACU-5A5, etc.;

amyloid vaccines such as AN-1792, ACC-001, etc.;

neuroprotective agents such as Cerebrolysin, AL-108, AL-208, Huperzine A, etc.;

L-type calcium channel antagonists such as MEM-1003, etc.;

nicotinic receptor antagonists, such as AZD3480, GTS-21, etc.;

nicotinic receptor agonists, such as MEM 3454, Nefiracetam, etc.;

peroxisome proliferator-activated receptor (PPAR) gamma agonists such as Avandia® (Rosglitazone), etc.;

phosphodiesterase IV (PDE4) inhibitors, such as MK-0952, etc.;

hormone replacement therapy such as estrogen (Premarin), etc.;

monoamine oxidase (MAO) inhibitors such as NS2330, Rasagiline (Azilect®), TVP-1012, etc.;

AMPA receptor modulators such as Ampalex (CX 516), etc.;

nerve growth factors or NGF potentiators, such as CERE-110 (AAV-NGF), T-588, T-817MA, etc.;

agents that prevent the release of luteinizing hormone (LH) by the pituitary gland, such as leuoprolide (VP-4896), etc.;

GABA receptor modulators such as AC-3933, NGD 97-1, CP-457920, etc.;

benzodiazepine receptor inverse agonists such as SB-737552 (S-8510), AC-3933, etc.;

noradrenaline-releasing agents such as T-588, T-817MA, etc.

It is to be understood that combination of compounds according to the invention, or for use according to the invention, with Alzheimer's agents is not limited to the examples described herein, but may include combination with any agent useful for the treatment of Alzheimer's disease. Combination of compounds according to the invention, or for use according to the invention, and other Alzheimer's agents may be administered separately or in conjunction. The administration of one agent may be prior to, concurrent to, or subsequent to the administration of other agent(s).

As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a subject that is predisposed to such disease or disorder. The terms "administration of" and "administering" a compound should be understood to mean providing a compound of the invention or a prodrug of a compound of the invention to to the subject.

The term "composition" as used herein is intended to encompass a product comprising the specified ingredients in the specified amounts, as well as any product which results, directly or indirectly, from combination of the specified ingredients in the specified amounts. Such term is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

Compounds according to the invention, or for use according to the invention, may be provided alone or in combination with other compounds in the presence of a liposome, an adjuvant, or any pharmaceutically acceptable carrier, diluent or excipient, in a form suitable for administration to a subject such as a mammal, for example, humans, cattle, sheep, etc. If desired, treatment with a compound according to the invention may be combined with more traditional and existing therapies for the therapeutic indications described herein. Compounds according to the invention may be provided chronically or intermittently. "Chronic" administration refers to administration of the compound(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Pharmaceutically acceptable carrier, diluent or excipient" may include, without limitation, any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier that has been approved, for example, by the United States Food and Drug Administration or other governmental agency as being acceptable for use in humans or domestic animals.

A compound of the present invention may be administered in the form of a pharmaceutically acceptable salt. In such cases, pharmaceutical compositions in accordance with this invention may comprise a salt of such a compound, preferably a physiologically acceptable salt, which are known in the art. In some embodiments, the term "pharmaceutically acceptable salt" as used herein means an active ingredient comprising compounds of formula I used in the form of a salt thereof, particularly where the salt form confers on the active ingredient improved pharmacokinetic properties as compared to the free form of the active ingredient or other previously disclosed salt form.

A "pharmaceutically acceptable salt" may include both acid and base addition salts. A "pharmaceutically acceptable acid addition salt" refers to those salts which retain the biological effectiveness and properties of the free bases, which are not biologically or otherwise undesirable, and which may be formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

A "pharmaceutically acceptable base addition salt" refers to those salts which may retain the biological effectiveness and properties of the free acids, which may not be biologically or otherwise undesirable. These salts may be prepared from addition of an inorganic base or an organic base to the free acid. Salts derived from inorganic bases may include, but are not limited to, the sodium, potassium, lithium, ammonium, calcium, magnesium, iron, zinc, copper, manganese, aluminum salts and the like. Preferred inorganic salts may be the ammonium, sodium, potassium, calcium, and magnesium salts. Salts derived from organic bases may include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases may be isopropylamine, diethylamine, ethanolamine, trimethylamine, dicyclohexylamine, choline and caffeine.

Thus, the term "pharmaceutically acceptable salt" encompasses all acceptable salts including but not limited to acetate, lactobionate, benzenesulfonate, laurate, benzoate, malate, bicarbonate, maleate, bisulfate, mandelate, bitartarate, mesylate, borate, methylbromide, bromide, methylnitrite, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutame, stearate, glycollylarsanilate, sulfate, hexylresorcinate, subacetate, hydradamine, succinate, hydrobromide, tannate, hydrochloride, tartrate, hydroxynaphthoate, teoclate, iodide, tosylate, isothionate, triethiodide, lactate, panoate, valerate, and the like.

Pharmaceutically acceptable salts of a compound of the present invention may be used as a dosage for modifying solubility or hydrolysis characteristics, or may be used in sustained release or prodrug formulations. Also, pharmaceutically acceptable salts of a compound of this invention may include those formed from cations such as sodium, potassium, aluminum, calcium, lithium, magnesium, zinc, and from bases such as ammonia, ethylenediamine, N-methylglutamine, lysine, arginine, ornithine, choline, N,N'-dibenzylethylene-diamine, chloroprocaine, diethanolamine, procaine, N-benzylphenethyl-amine, diethylamine, piperazine, tris(hydroxymethyl)aminomethane, and tetramethylammonium hydroxide.

Pharmaceutical formulations may typically include one or more carriers acceptable for the mode of administration of the preparation, be it by injection, inhalation, topical administration, lavage, or other modes suitable for the selected treatment. Suitable carriers may be those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non-water soluble compounds such as those used for vitamin K. For enteral administration, the compound may be administered in a tablet, capsule or dissolved in liquid form. The table or capsule may be enteric coated, or in a formulation for sustained release. Many suitable formulations are known, including, polymeric or protein microparticles encapsulating a compound to be released, ointments, gels, hydrogels, or solutions which can be used topically or locally to administer a compound. A sustained release patch or implant may be employed to provide release over a prolonged period of time. Many techniques known to skilled practitioners are described in *Remington: the Science & Practice of Pharmacy* by Alfonso Gennaro, $20^{th}$ ed., Williams & Wilkins, (2000). Formulations for parenteral administration may, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of a compound. Other potentially useful parenteral delivery systems for modulatory compounds may include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

A compound or a pharmaceutical composition according to the present invention may be administered by oral or non-oral, e.g., intramuscular, intraperitoneal, intravenous, intracisternal injection or infusion, subcutaneous injection, transdermal or transmucosal routes. In some embodiments, a compound or pharmaceutical composition in accordance with this invention or for use in this invention may be administered by means of a medical device or appliance such as an implant, graft, prosthesis, stent, etc. Implants may be devised which are intended to contain and release such compounds or compositions. An example would be an implant made of a polymeric material adapted to release the compound over a period of time. A compound may be administered alone or as a mixture with a pharmaceutically acceptable carrier e.g., as solid formulations such as tablets, capsules, granules, powders, etc.; liquid formulations such as syrups, injections, etc.; injections, drops, suppositories, pessaryies. In some embodiments, compounds or pharmaceutical compositions in accordance with this invention or for use in this invention may be administered by inhalation spray, nasal, vaginal, rectal, sublingual, or topical routes and may be formulated, alone or together, in suitable dosage unit formulations containing conventional non-toxic pharmaceutically acceptable carriers, adjuvants and vehicles appropriate for each route of administration.

A compound of the invention may be used to treat animals, including mice, rats, horses, cattle, sheep, dogs, cats, and monkeys. However, a compound of the invention may also be used in other organisms, such as avian species (e.g., chickens). One or more of the compounds of the invention may also be effective for use in humans. The term "subject" or alternatively referred to herein as "patient" is intended to be referred to an animal, preferably a mammal, most preferably a human being, male or female, including an elderly human being, who has been the object of treatment, observation or experiment. However, one or more of the compounds, methods and pharmaceutical compositions of the present invention may be used in the treatment of animals. Accordingly, as used herein, a "subject" may be a human, non-human primate, rat, mouse, cow, horse, pig, sheep, goat, dog, cat, etc. The subject may be suspected of having or at risk for having a condition that may require modulation of O-GlcNAcase activity.

An "effective amount" of a compound according to the invention may include a therapeutically effective amount or a prophylactically effective amount. A "therapeutically effective amount" refers to an amount effective, at dosages and for periods of time necessary, to achieve the desired therapeutic result, such as inhibition of an O-GlcNAcase, elevation of O-GlcNAc levels, inhibition of tau phosphorylation, or any condition described herein. A therapeutically effective amount of a compound may vary according to factors such as the disease state, age, sex, and weight of the individual, and the ability of the compound to elicit a desired response in the individual. Dosage regimens may be adjusted to provide the optimum therapeutic response. A therapeutically effective amount may also be one in which any toxic or detrimental effects of the compound are outweighed by the therapeutically beneficial effects. A "prophylactically effective amount" may refer to an amount effective, at dosages and for periods of time necessary, to achieve the desired prophylactic result, such as inhibition of an O-GlcNAcase, elevation of O-GlcNAc levels, inhibition of tau phosphorylation, or any condition described herein. Typically, a prophylactic dose may be used in subjects prior to or at an earlier stage of disease, so that a prophylactically effective amount may be less than a therapeutically effective amount. A suitable range for therapeutically or prophylactically effective amounts of a compound may be any integer from 0.1 nM-0.1 M, 0.1 nM-0.05 M, 0.05 nM-15 μM or 0.01 nM-10 μM.

In alternative embodiments, in the treatment or prevention of conditions which may require modulation of O-GlcNAcase activity, an appropriate dosage level may generally be about 0.01 to 500 mg per kg subject body weight per day, and may be administered in singe or multiple doses. In some embodiments, the dosage level may be about 0.1 to about 250 mg/kg per day. It will be understood that the specific dose level and frequency of dosage for any particular patient may be varied and may depend upon a variety of factors including the activity of the specific compound used, the metabolic stability and length of action of that compound, the age, body weight, general health, sex, diet, mode and time of administration, rate of excretion, drug combination, the severity of the particular condition, and the patient undergoing therapy.

It is to be noted that dosage values may vary with the severity of the condition to be alleviated. For any particular subject, specific dosage regimens may be adjusted over time according to the individual need and the professional judgement of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage. In general, compounds of the invention should be used without causing substantial toxicity, and as described herein, one or more of the compounds may exhibit a suitable safety profile for therapeutic use. Toxicity of a compound of the invention may be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances however, such as in severe disease conditions, it may be necessary to administer substantial excesses of the compositions.

A compound of the present invention may be used in screening assays for compounds which modulate the activity of glycosidase enzymes, preferably the O-GlcNAcase enzyme. The ability of a test compound to inhibit O-GlcNAcase-dependent cleavage of O-GlcNAc from a model substrate may be measured using any assays, as described herein or known to one of ordinary skill in the art. For example, a fluoresence or UV-based assay known in the art may be used. A "test compound" may be any naturally-occurring or artificially-derived chemical compound. Test compounds may include, without limitation, peptides, polypeptides, synthesised organic molecules, naturally occurring organic molecules, and nucleic acid molecules. A test compound may "compete" with a known compound such as a compound of the present invention by, for example, interfering with inhibition of O-GlcNAcase-dependent cleavage of O-GlcNAc or by interfering with any biological response induced by a compound of the present invention.

Generally, a test compound may exhibit any value between 10% and 200%, or over 500%, modulation when compared to a compound of the present invention or other reference compound. For example, a test compound may exhibit at least any positive or negative integer from 10% to 200% modulation, or at least any positive or negative integer from 30% to 150% modulation, or at least any positive or negative integer from 60% to 100% modulation, or any positive or negative integer over 100% modulation. A compound that is a negative modulator may in general decrease modulation relative to a known compound, while a compound that is a positive modulator may in general increase modulation relative to a known compound.

In general, test compounds may be identified from large libraries of both natural products or synthetic (or semisynthetic) extracts or chemical libraries according to methods known in the art. Those skilled in the field of drug discovery and development will understand that the precise source of test extracts or compounds is not critical to the method(s) of the invention. Accordingly, virtually any number of chemical extracts or compounds may be screened using the exemplary methods described herein. Examples of such extracts or compounds may include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, that may include, without limitation, saccharide-, lipid-, peptide-, and nucleic acid-based compounds. Synthetic compound libraries are commercially available. Alternatively, libraries of natural compounds in the form of bacterial, fungal, plant, and animal extracts are commercially available from a number of sources, including Biotics (Sussex, UK), Xenova (Slough, UK), Harbor Branch Oceanographic Institute (Ft. Pierce, Fla., USA), and PharmaMar, MA, USA. In addition, natural and synthetically produced libraries may be produced, if desired, according to methods known in the art, e.g., by standard extraction and fractionation methods. Furthermore, if desired, any library or compound may be readily modified using standard chemical, physical, or biochemical methods.

When a crude extract is found to modulate inhibition of O-GlcNAcase-dependent cleavage of O-GlcNAc, or any biological response induced by a compound of formula (I), further fractionation of the positive lead extract may be necessary to isolate chemical constituents responsible for the observed effect. Thus, the goal of the extraction, fractionation, and purification process is the careful characterization and identification of a chemical entity within the crude extract having O-GlcNAcase-inhibitory activities. The same assays described herein for the detection of activities in mixtures of compounds may be used to purify the active component and to test derivatives thereof. Methods of fractionation and purification of such heterogeneous extracts are known in the art. If desired, compounds shown to be useful agents for treatment may be chemically modified according to methods known in the art. Compounds identified as being of therapeutic, prophylactic, diagnostic, or other value may be subsequently analyzed using a suitable animal model, as described herein on known in the art.

In some embodiments, one or more of the compounds may be useful in the development of animal models for studying diseases or disorders that may be related to deficiencies in O-GlcNAcase, over-expression of O-GlcNAcase, accumulation of O-GlcNAc, depletion of O-GlcNAc, and for studying treatment of diseases and disorders that may be related to deficiency or over-expression of O-GlcNAcase, or accumulation or depletion of O-GlcNAc. Such diseases and disorders may include neurodegenerative diseases, including Alzheimer's disease, and cancer.

Various alternative embodiments and examples of the invention are described herein. These embodiments and examples are illustrative and should not be construed as limiting the scope of the invention.

Several methods for preparing the compounds of this invention are illustrated in the following Schemes and Examples. Starting materials are made according to procedures known in the art or as illustrated herein. The following abbreviations may be used herein:

AIBN (2,2'-Azobisisobutyronitrile)
BCl$_3$ (Boron Trichloride)
BOC (tert-Butylcarbamate)
Bu$_3$SnH (Tributyltin hydride)
CDCl$_3$ (Deuterochloroform)
DAST (Diethylamino)sulfur trifluoride)
DCM (Dichloromethane)
DMF (Dimethylformamide)
DMP (Dess-Martin Periodinane)
EDC (1-Ethyl-3(3-Dimethlaminopropyl carbodiimide HCl)
LiHMDS (Lithium hexamethyldisilylazide)
NBS (N-Bromosuccinimide)
Pd(PPh$_3$)$_4$ (Tetrakis(Triphenylphosphine) palladium (0))
PMB (Para-methoxybenzyl)
TBAB (Tetrabutyl ammonium bromide)
TBAF (Tetra-n-butyl ammonium fluoride)
TEA (Triethylamine)
TEMPO ((2,2,6,6-Tetramethylpiperidin-1-yl)oxyl)
THF (Tetrahydrofuran)
TFA (Trifluoroacetic acid)
TLC (Thin layer chromatography)
TMS (Trimethylsilyl)

The compounds of the present invention can be prepared in a variety of fashions. In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. Because the schemes are an illustration, the invention should not be construed as being limited by the chemical reactions and conditions expressed. The preparation of the various starting materials used herein is well within the skill of a person versed in the art. The following examples are provided so that the invention might be more fully understood. These examples are illustrative only and should not be construed as limiting the invention in any way. Absolute stereochemistry of separate stereoisomers in the examples and intermediates are not determined unless stated otherwise in an example or explicitly in the nomenclature.

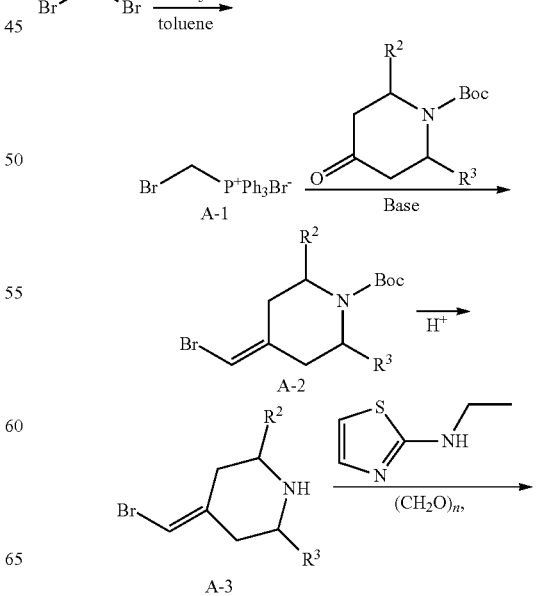

SCHEME A

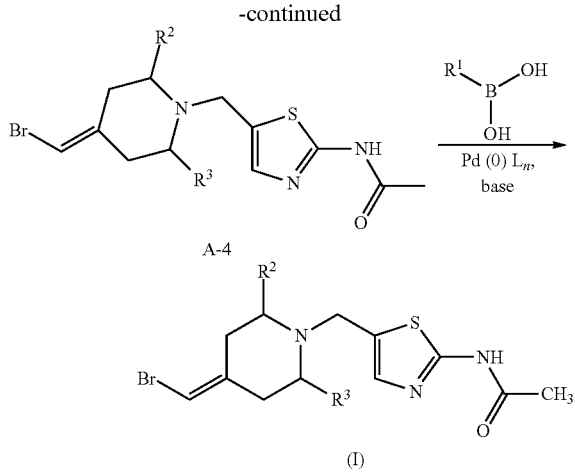

Compounds of the formula (I) are prepared from tert-butyl 4-oxopiperidine-1-carboxylate by addition of the phosphonium ylide derived from dibromomethane to afford the corresponding olefin (A-2). Acidic deprotection of the Boc group may be followed by iminium formation with paraformaldehyde, followed by nucleophilic addition of N-acylaminothiazole to afford the substituted piperidine (A-4). Finally, the vynilic bromide is coupled to an appropriately substituted aryl or heteroaryl boronic acid via a Suzuki reaction to provide compounds of the formula (I).

Example 1

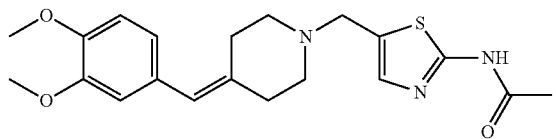 [SMILES: COc1ccc(C=C2CCN(Cc3cnc(NC(C)=O)s3)CC2)cc1OC]

N-(5-((4-(3,4-dimethoxybenzylidene)piperidin-1-yl)methyl)thiazol-2-yl)acetamide

Step 1: Bromomethyl)triphenylphosphonium bromide

A solution of PPh$_3$ (200 g, 0.76 mol) and dibromomethane (132 g, 0.77 mol) in toluene (1.5 L) was heated at 100° C. for 12 hours. The mixture was cooled to ambient temperature, and the solids were collected by filtration and washed with ether (3×400 mL) to afford the title compound as a solid (236 g); $^1$H NMR (300 MHz, CDCl$_3$) δ 7.75-7.98 (m, 15H), 5.85 (d, J=5.7 Hz, 2H).

Step 2: Tert-butyl 4-(bromomethylene)piperidine-1-carboxylate

To a suspension of (bromomethyl)triphenylphosphonium bromide (155 g, 0.36 mol) in anhydrous THF (1.2 L) at −20° C. under nitrogen atmosphere was added 1N solution of LiHMDS (460 mL, 0.46 mol) in THF dropwise. After additional 30 minutes, tert-butyl 4-oxopiperidine-1-carboxylate (50 g, 0.25 mol) was added in one portion. The resulting solution was stirred for 1 hour at 0° C., and then quenched with saturated aqueous ammonium chloride solution (600 mL) and diluted with water (1.5 L). The aqueous layer was extracted with ethyl acetate (3×500 mL). The combined organic layer was washed with brine (3×200 mL), dried over anhydrous sodium sulfate, filtered and concentrated under vacuum. The crude residue was purified by a silica gel column, eluted with 2%-10% ethyl acetate in petroleum ether to give the title compound. (ES, m/z): [M+H]$^+$ 276.0 and 278.0; $^1$H NMR (300 MHz, CDCl$_3$) δ 6.00 (s, 1H), 3.46-3.40 (m, 4H), 2.41-2.38 (m, 2H), 2.26-2.23 (m, 2H), 1.48 (s, 9H).

Step 3: N-(5-((4-(bromomethylene)piperidin-1-yl)methyl)thiazol-2-yl)acetamide A solution of tert-butyl 4-(bromomethylene)piperidine-1-carboxylate (35 g, 0.13 mol) in dichloromethane (200 mL) was treated with TFA (70 mL) for 2 hours at room temperature. Volatiles were distilled out to give an oil, which was dissolved into acetic acid (200 mL) followed by the addition of N-(thiazol-2-yl)acetamide (27.7 g, 0.2 mol). The resulting solution was heated to 90-95° C. and paraformaldehyde (24 g, 0.8 mol) was added to the solution in several batches over 1 hour. After additional 2 hours, the volatiles were distilled out to give a residue, which was dissolved into dichloromethane (200 mL) and neutralized with saturated aqueous sodium bicarbonate. The aqueous layer was extracted with dichloromethane (3×150 mL), and the combined organic layer was dried over anhydrous sodium sulfate, filtered and concentrated under vacuum. The crude residue was purified by a silica gel column, eluted with 1%-2% methanol in dichloromethane to give the title compound; (ES, m/z): [M+H]$^+$ 330.0 and 332.0; $^1$H NMR (300 MHz, CDCl$_3$) δ 7.56 (s, 1H), 6.16 (s, 1H), 4.34 (s, 2H), 3.38-3.00 (m, 4H), 2.86-2.78 (m, 2H), 2.64-2.54 (m, 2H), 2.36 (s, 3H).

Step 4: N-(5-((4-(3,4-dimethoxybenzylidene)piperidin-1-yl)methyl)thiazol-2-yl)acetamide To a solution of N-(5-((4-(bromomethylene)piperidin-1-yl)methyl)thiazol-2-yl)acetamide (5 g, 15 mmol) in 1,4-dioxane (150 mL) and water (5 mL) was added 3,4-dimethoxyphenylboronic acid (3.2 g, 18 mmol), Pd(PPh$_3$)$_4$ (1.7 g, 1.5 mmol) and potassium carbonate (4.1 g, 30 mmol). The resulting mixture was stirred for 4 hours at 85-90° C. under nitrogen atmosphere. The reaction was cooled to ambient temperature, diluted with water (100 mL), and extracted with ethyl acetate (3×150 mL). The combined organic layer was dried over anhydrous sodium sulfate, filtered and concentrated under vacuum. The crude residue was purified by a silica gel column, eluted with 1%-2% methanol in dichloromethane to afford the title compound; (ES, m/z): [M+H]$^+$ 388.0; $^1$H NMR (300 MHz, CDCl$_3$) S 12.11 (s, 1H), 7.27 (s, 1H), 6.84-6.73 (m, 3H), 6.23 (s, 1H), 3.88 (s, 3H), 3.87 (s, 3H), 3.30 (s, 2H), 2.59-2.40 (m, 8H), 2.33 (s, 3H).

Example 2 and Example 3

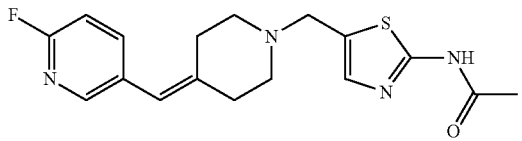

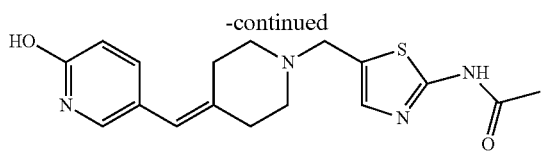

N-(5-((4-((6-fluoropyridin-3-yl)methylene)piperidin-1-yl)methyl)thiazol-2-yl)acetamide and N-(5-((4-((6-hydroxypyridin-3-yl)methylene)piperidin-1-yl)methyl)thiazol-2-yl)acetamide Step 1: tert-butyl 4-((6-fluoropyridin-3-yl)methylene)piperidine-1-carboxylate To a solution of tert-butyl 4-(bromomethylene)piperidine-1-carboxylate (17.4 g, 63 mmol) in 1,4-dioxane (100 mL) was added 6-fluoropyridin-3-ylboronic acid (11 g, 76 mmol), Pd(PPh$_3$)$_4$ (3.6 g, 3 mmol), potassium carbonate (26.2 g, 190 mmol) and water (60 mL). The mixture was stirred for 1 hour at 90° C. under nitrogen atmosphere. After cooling to room temperature, the reaction was diluted with water (100 mL) and extracted with ethyl acetate (3×100 mL). The combined organic layer was dried over anhydrous sodium sulfate and concentrated under reduced pressure to give a residue, which was purified by a silica gel column, eluted with 10% ethyl acetate in petroleum ether to afford tert-butyl 4-((6-fluoropyridin-3-yl)methylene)piperidine-1-carboxylate as an oil (17 g); (ES, m/z): [M+H]$^+$ 293.0; $^1$H NMR (300 MHz, CDCl$_3$) 8.04 (d, J=1.8 Hz, 1H), 7.56-7.62 (m, 1H), 6.88-6.91 (m, 1H), 6.27 (s, 1H), 3.52 (t, J=5.7 Hz, 2H), 3.42 (t, J=5.7 Hz, 2H), 2.34-2.41 (m, 4H), 1.48 (s, 9H).

Step 2: 2-fluoro-5-(piperidin-4-ylidenemethyl)pyridine

A solution of tert-butyl 4-((6-fluoropyridin-3-yl)methylene)piperidine-1-carboxylate (17 g, 58 mmol) in dichloromethane (100 mL) was treated with TFA (66.4 g, 582 mmol) for 1 hour at room temperature. Volatiles were distilled out to give a residue, which was dissolved into dichloromethane (50 mL) and neutralized with saturated sodium bicarbonate aqueous solution. The aqueous layer was extracted with dichloromethane (3×30 mL), and the combined organic layer was dried over anhydrous sodium sulfate, filtered and concentrated under reduced pressure to give the title compound as a solid (10.6 g); (ES, m/z): [M+H]$^-$ 293.0; $^1$H NMR (300 MHz, CDCl$_3$) δ 8.04 (t, J=0.9 Hz, 1H), 7.56-7.62 (m, 1H), 6.90-6.94 (m, 1H), 6.34 (s, 1H), 5.71 (s, 1H), 3.19 (t, J=6.0 Hz, 2H), 3.07 (t, J=6.0 Hz, 2H), 2.58-2.63 (m, 4H).

Step 3: (5-((1-((2-acetamidothiazol-5-yl)methyl)piperidin-4-ylidene)methyl)-2-oxopyridin-1(2H)-yl) methyl acetate (16-3) and N-(5-((4-((6-fluoropyridin-3-yl)methylene)piperidin-1-yl)methyl)thiazol-2-yl)acetamide (Example 2)

Paraformaldehyde (15.6 g, 520 mmol) was added to a solution of 2-fluoro-5-(piperidin-4-ylidenemethyl) pyridine (10 g, 52 mmol) and N-(thiazol-2-yl)acetamide (11.1 g, 78 mmol) in acetic acid (150 mL) at 100° C. in several portions. After additional 30 min at 100° C., volatiles were distilled out to give a residue, which was dissolved into dichloromethane (50 mL) and neutralized with saturated sodium bicarbonate aqueous solution (30 mL). The aqueous layer was extracted with dichloromethane (3×50 mL), and the combined organic layer was dried over anhydrous sodium sulfate, filtered and concentrated. The crude residue was purified by a silica gel column, eluted with 1%-2% methanol in dichloromethane to give N-(5-((4-((6-fluoropyridin-3-yl)methylene)piperidin-1-yl)methyl)thiazol-2-yl)acetamide as a solid (3.3 g). (ES, m/z): [M+H]$^+$ 347.0; $^1$H NMR (300 MHz, CDCl$_3$) δ 11.82 (s, 1H), 8.03 (d, J=1.8 Hz, 1H), 7.54-7.61 (m, 1H), 7.21 (s, 1H), 6.86-6.91 (m, 1H), 6.18 (s, 1H), 3.72 (s, 2H), 2.58-2.60 (m, 2H), 2.42-2.47 (m, 6H), 2.31 (s, 3H), and also (5-((1-((2-acetamidothiazol-5-yl)methyl)piperidin-4-ylidene)methyl)-2-oxopyridin-1(2H)-yl) methyl acetate as a solid (10.8 g); (ES, m/z): [M+H]$^+$ 417.0; $^1$H NMR (300 MHz, CD$_3$OD) δ 7.56 (d, J=2.4 Hz, 1H), 7.45 (dd, J$_1$=2.4 Hz, J$_2$=6.9 Hz 1H), 7.24 (s, 1H), 6.53 (d, J=9.3 Hz, 1H), 6.01 (s, 1H), 5.87 (s, 2H), 3.73 (s, 2H), 2.60-2.58 (m, 2H), 2.52-2.48 (m, 4H), 2.45-2.38 (m, 2H), 2.21 (s, 3H), 2.04 (s, 3H).

N-(5-((4-((6-hydroxypyridin-3-yl)methylene)piperidin-1-yl)methyl)thiazol-2-yl)acetamide (Example 3)

A solution of (5-((1-((2-acetamidothiazol-5-yl)methyl)piperidin-4-ylidene)methyl)-2-oxopyridin-1(2H)-yl)methyl acetate (from Step 3) (1 g, 2.40 mmol) in methanol (100 mL) was treated with potassium carbonate (200 mg, 1.45 mmol) for 2 hours at 25° C. The reaction was quenched by the addition of acetic acid (1 mL) and concentrated under vacuum. The crude residue was purified by a silica gel column, eluted with 1%-5% methanol in dichloromethane to give the title compound as a solid (0.6 g, 73%); (ES, m/z): [M+H]$^+$ 345.0; $^1$H NMR (300 MHz, CD$_3$OD) δ 7.50 (dd, J=2.4 Hz, J$_2$=7.5 Hz 1H), 7.24 (s, 2H), 6.53 (d, J=9.6 Hz, 1H), 6.04 (s, 1H), 3.73 (s, 2H), 2.59-2.55 (m, 2H), 2.48-2.47 (m, 4H), 2.41-2.37 (m, 2H), 2.20 (s, 3H).

TABLE 1

The following compounds were prepared according to the general procedure provided in Scheme A, Example 1, 2, 3 and procedures herein. The starting materials are prepared as described herein, commercially available, or may be prepared from commercially available reagents using conventional reactions well known in the art.

| Ex. | Structure | Name | Mass [M + H] |
|---|---|---|---|
| 4 | 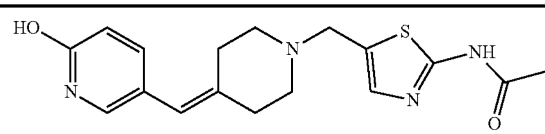 | N-[5-({4-[(4-hydroxyphenyl)methylidene]-piperidin-1-yl}methyl)-1,3-thiazol-2-yl]acetamide | Calc'd 344, found 344 |

TABLE 1-continued

The following compounds were prepared according to the general procedure
provided in Scheme A, Example 1, 2, 3 and procedures herein. The starting materials are
prepared as described herein, commercially available, or may be prepared from commercially
available reagents using conventional reactions well known in the art.

| Ex. | Structure | Name | Mass [M + H] |
|---|---|---|---|
| 5 | 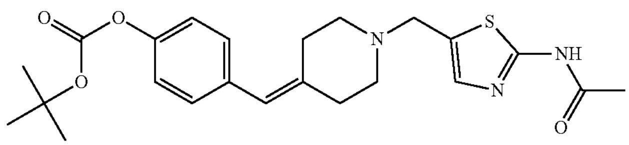 [SMILES: CC(=O)Nc1ncc(CN2CCC(=Cc3ccc(OC(=O)OC(C)(C)C)cc3)CC2)s1] | 4-((1-((2-acetamidothiazol-5-yl)methyl)piperidin-4-ylidene)methyl)phenyl tert-butyl carbonate | Calc'd 444. found 444 |
| 6 | 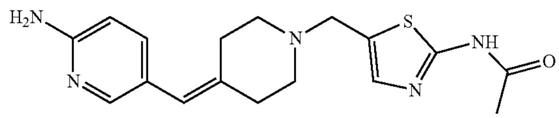 [SMILES: CC(=O)Nc1ncc(CN2CCC(=Cc3ccc(N)nc3)CC2)s1] | N-[5-({4-[(6-aminopyridin-3-yl)methylidene]piperidin-1-yl}methyl)-1,3-thiazol-2-yl]acetamide | Calc'd 344, found 344 |
| 7 | 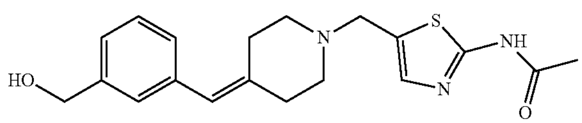 [SMILES: CC(=O)Nc1ncc(CN2CCC(=Cc3cccc(CO)c3)CC2)s1] | N-(5-((4-(3-(hydroxymethyl)benzylidene)piperidin-1-yl)methyl)thiazol-2-yl)acetamide | Calc'd 358, found 358 |
| 8 | 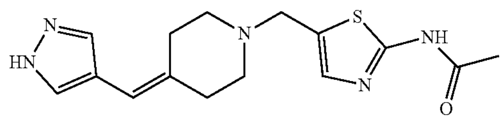 [SMILES: CC(=O)Nc1ncc(CN2CCC(=Cc3cn[nH]c3)CC2)s1] | N-(5-((4-((1H-pyrazol-4-yl)methylene)piperidin-1-yl)methyl)thiazol-2-yl)acetamide | Calc'd 318, found 318 |
| 9 | 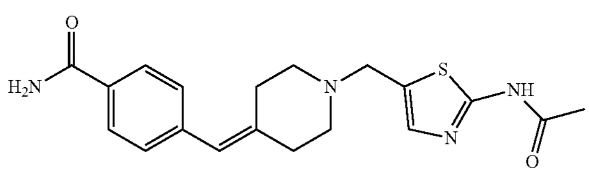 [SMILES: CC(=O)Nc1ncc(CN2CCC(=Cc3ccc(C(N)=O)cc3)CC2)s1] | 4-((1-((2-acetamidothiazol-5-yl)methyl)-piperidin-4-ylidene)methyl)benzamide | Calc'd 371, found 371 |
| 10 | 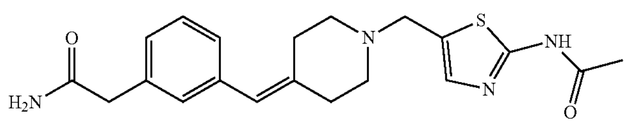 [SMILES: CC(=O)Nc1ncc(CN2CCC(=Cc3cccc(CC(N)=O)c3)CC2)s1] | 2-(3-((1-((2-acetamidothiazol-5-yl)methyl)-piperidin-4-ylidene)methyl)phenyl)acetamide | Calc'd 385, found 385 |
| 11 | | N-(5-((4-(4-(trifluoromethoxy)benzylidene)-piperidin-1-yl)methyl)thiazol-2-yl)acetamide | Calc'd 412, found 412 |
| 11 | | N-(5-((4-(4-ethylbenzylidene)piperidin-1-yl)methyl)thiazol-2-yl)acetamide | Calc'd 356, found 356 |
| 13 | 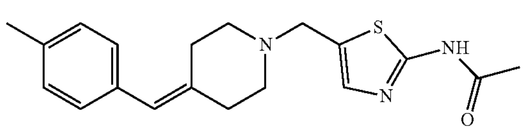 [SMILES: CC(=O)Nc1ncc(CN2CCC(=Cc3ccc(C)cc3)CC2)s1] | N-(5-((4-(4-methylbenzylidene)piperidin-1-yl)methyl)thiazol-2-yl)acetamide | Calc'd 342, found 342 |
| 14 | 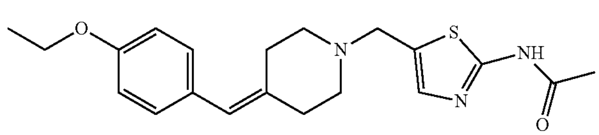 [SMILES: CCOc1ccc(C=C2CCN(Cc3cnc(NC(C)=O)s3)CC2)cc1] | N-(5-((4-(4-ethoxybenzylidene)piperidin-1-yl)methyl)thiazol-2-yl)acetamide | Calc'd 372, found 372 |

TABLE 1-continued

The following compounds were prepared according to the general procedure
provided in Scheme A, Example 1, 2, 3 and procedures herein. The starting materials are
prepared as described herein, commercially available, or may be prepared from commercially
available reagents using conventional reactions well known in the art.

| Ex. | Structure | Name | Mass [M + H] |
|---|---|---|---|
| 15 | 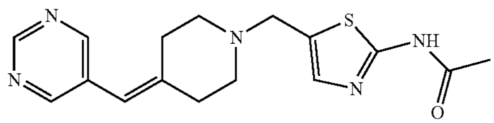 [SMILES: CC(=O)Nc1ncc(CN2CCC(=Cc3cncnc3)CC2)s1] | N-(5-((4-(pyrimidin-5-ylmethylene)piperidin-1-yl)methyl)thiazol-2-yl)acetamide | Calc'd 330, found 330 |
| 16 | 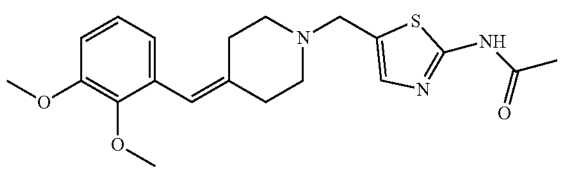 [SMILES: COc1cccc(C=C2CCN(Cc3cnc(NC(C)=O)s3)CC2)c1OC] | N-[5-({4-[(2,3-dimethoxyphenyl)methylidene]piperidin-1-yl}methyl)-1,3-thiazol-2-yl]acetamide | Calc'd 388, found 388 |
| 17 | 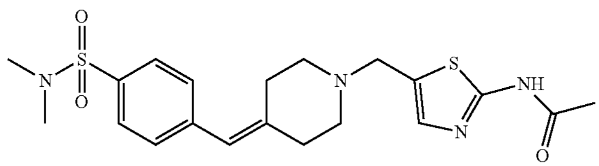 [SMILES: CC(=O)Nc1ncc(CN2CCC(=Cc3ccc(S(=O)(=O)N(C)C)cc3)CC2)s1] | N-(5-((4-(4-(N,N-dimethylsulfamoyl)benzylidene)piperidin-1-yl)methyl)thiazol-2-yl)acetamide | Calc'd 435, found 435 |
| 18 | 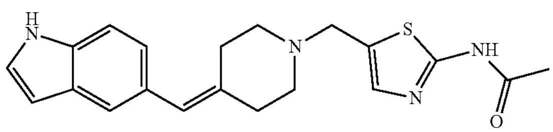 [SMILES: CC(=O)Nc1ncc(CN2CCC(=Cc3ccc4[nH]ccc4c3)CC2)s1] | N-(5-{[4-(1H-indol-5-ylmethylidene)piperidin-1-yl]methyl}-1,3-thiazol-2-yl)acetamide | Calc'd 367, found 367 |
| 19 | 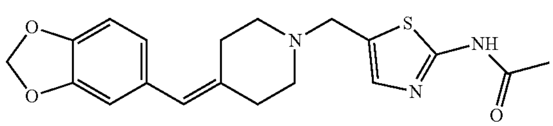 [SMILES: CC(=O)Nc1ncc(CN2CCC(=Cc3ccc4c(c3)OCO4)CC2)s1] | N-(5-{[4-(1,3-benzodioxol-5-ylmethylidene)piperidin-1-yl]methyl}-1,3-thiazol-2-yl)acetamide | Calc'd 372, found 372 |
| 20 | 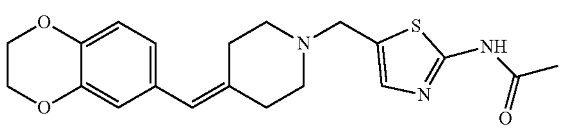 [SMILES: CC(=O)Nc1ncc(CN2CCC(=Cc3ccc4c(c3)OCCO4)CC2)s1] | N-(5-{[4-(2,3-dihydro-1,4-benzodioxin-6-ylmethylidene)piperidin-1-yl]methyl}-1,3-thiazol-2-yl)acetamide | Calc'd 386, found 386 |
| 21 | 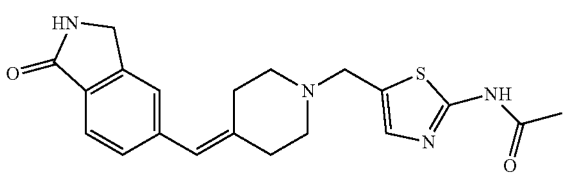 [SMILES: CC(=O)Nc1ncc(CN2CCC(=Cc3ccc4c(c3)CNC4=O)CC2)s1] | N-(5-((4-((1-oxoisoindolin-5-yl)methylene)piperidin-1-yl)methyl)thiazol-2-yl)acetamide | Calc'd 383, found 383 |
| 22 | 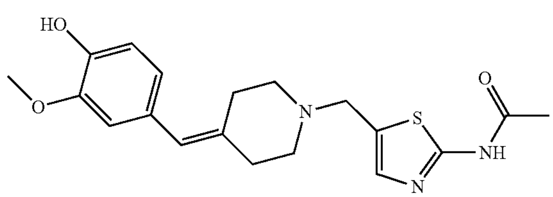 [SMILES: COc1cc(C=C2CCN(Cc3cnc(NC(C)=O)s3)CC2)ccc1O] | N-[5-({4-[(4-hydroxy-3-methoxyphenyl)methylidene]piperidin-1-yl}methyl)-1,3-thiazol-2-yl]acetamide | Calc'd 374, found 374 |
| 23 | 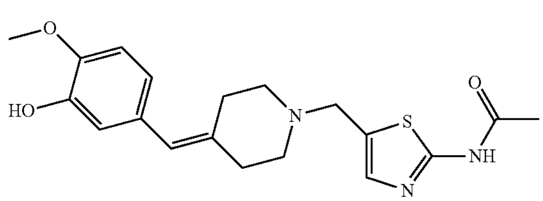 [SMILES: COc1ccc(C=C2CCN(Cc3cnc(NC(C)=O)s3)CC2)cc1O] | N-[5-({4-[(3-hydroxy-4-methoxyphenyl)methylidene]piperidin-1-yl}methyl)-1,3-thiazol-2-yl]acetamide | Calc'd 374, found 374 |

TABLE 1-continued

The following compounds were prepared according to the general procedure provided in Scheme A, Example 1, 2, 3 and procedures herein. The starting materials are prepared as described herein, commercially available, or may be prepared from commercially available reagents using conventional reactions well known in the art.

| Ex. | Structure | Name | Mass [M + H] |
|---|---|---|---|
| 24 | 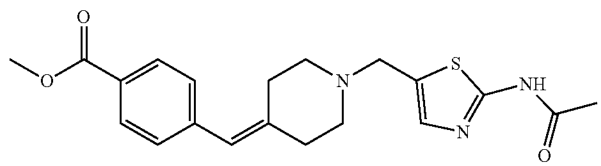 [SMILES: COC(=O)c1ccc(C=C2CCN(Cc3cnc(NC(C)=O)s3)CC2)cc1] | methyl 4-((1-((2-acetamidothiazol-5-yl)methyl)piperidin-4-ylidene)methyl)benzoate | Calc'd 386, found 386 |
| 25 | 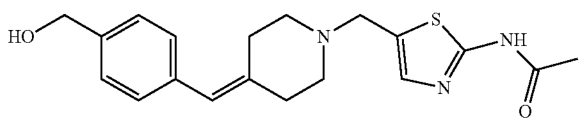 [SMILES: CC(=O)Nc1ncc(CN2CCC(=Cc3ccc(CO)cc3)CC2)s1] | N-{5-[(4-{[4-(hydroxymethyl)phenyl]methylidene}piperidin-1-yl)methyl]-1,3-thiazol-2-yl}acetamide | Calc'd 358, found 358 |

Example 26

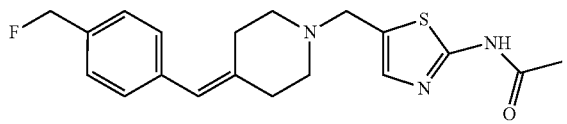 [SMILES: CC(=O)Nc1ncc(CN2CCC(=Cc3ccc(CF)cc3)CC2)s1]

N-(5-((4-(4-(fluoromethyl)benzylidene)piperidin-1-yl)methyl)thiazol-2-yl)acetamide To a solution of N-[5-[(4-[[4-(hydroxymethyl)phenyl]methylidene]piperidin-1-yl)methyl]-1,3-thiazol-2-yl]acetamide (Example 23) (80 mg, 0.22 mmol) in dichloromethane (20 mL) with stirring at −78° C. was added DAST (144 mg, 0.89 mmol) dropwise. The resulting solution was stirred while warming to ambient temperature over 4 h. The reaction was then quenched by the addition of 30 mL of saturated aqueous sodium bicarbonate. The resulting mixture was extracted with 3×20 mL of dichloromethane and the organic layers combined and dried over anhydrous sodium sulfate and concentrated under vacuum. The residue was applied onto a silica gel column with dichloromethane/methanol (10:1) to afford the title compound. (ES, m/z): [M+H]$^+$ 360; $^1$H NMR (300 MHz, CDCl$_3$) δ 11.52 (s, 1H), 7.23 (m, 5H), 6.26 (s, 1H), 5.32 (d, J=48 Hz, 2H), 3.63 (s, 2H), 2.65-2.39 (m, 8H), 2.28 (s, 3H).

TABLE 2

The following compounds were prepared according to the general procedure provided in Scheme A, Example 1, 2, 3 and procedures herein. The starting materials are prepared as described herein, commercially available, or may be prepared from commercially available reagents using conventional reactions well known in the art.

| Ex. | Structure | Name | Mass |
|---|---|---|---|
| 27 | 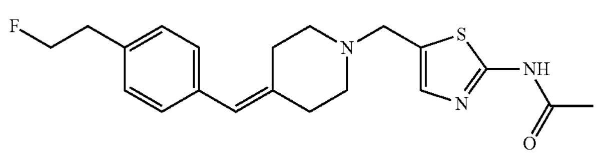 [SMILES: CC(=O)Nc1ncc(CN2CCC(=Cc3ccc(CCF)cc3)CC2)s1] | N-(5-((4-(4-(2-fluoroethyl)benzylidene)piperidin-1-yl)methyl)thiazol-2-yl)acetamide | Calc'd 372, found 372 |
| 28 | 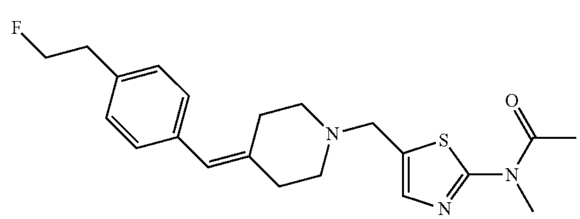 [SMILES: CC(=O)N(C)c1ncc(CN2CCC(=Cc3ccc(CCF)cc3)CC2)s1] | N-(5-((4-(4-(2-fluoroethyl)benzylidene)-piperidin-1-yl)methyl)thiazol-2-yl)-N-methylacetamide | Calc'd 388, Found 388 |

Example 29

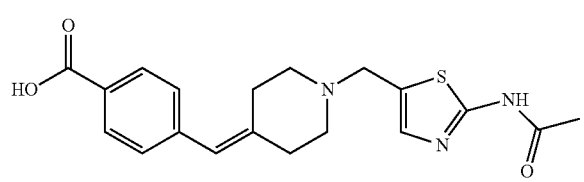 [SMILES: CC(=O)Nc1ncc(CN2CCC(=Cc3ccc(C(=O)O)cc3)CC2)s1]

4-[(1-{[2-(acetylamino)-1,3-thiazol-5-yl]methyl}piperidin-4-ylidene)methyl]benzoic acid To a solution of methyl 4-([1-[(2-acetamido-1,3-thiazol-5-yl)methyl]piperidin-4-ylidene]methyl)-benzoate (100 mg, 0.26 mmol) (Example 24) in methanol/water (20/5 mL) at 50° C. was added solid sodium hydroxide (41.6 mg, 1.04 mmol) with stirring. The resulting solution was stirred for 6 h while cooling to ambient temperature. The resulting mixture was concentrated under vacuum and suspended in water. The pH value of the solution was adjusted to 3-4 with 1 N HCl. The solids were collected by filtration, affording the title compound as its HCl salt. (ES, m/z): [M+H]$^+$ 372; $^1$H NMR (300 MHz, DMSO-D$_6$) δ 12.90 (s, 1H), 10.25 (s, 1H), 7.86 (d, J=8.4 Hz, 2H), 7.56 (s, 1H), 7.32 (d, J=8.4 Hz, 2H), 6.49 (s, 1H), 4.51 (s, 2H), 3.55-3.31 (m, 2H), 2.90-2.85 (m, 3H), 2.70-2.64 (m, 3H), 2.09 (s, 3H).

Example 30

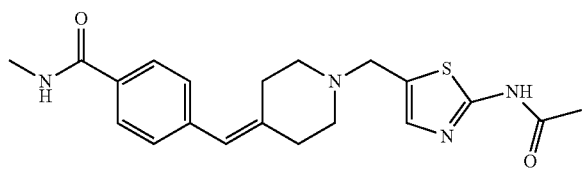 [SMILES: CNC(=O)c1ccc(C=C2CCN(Cc3cnc(NC(C)=O)s3)CC2)cc1]

4-[(1-{[2-(acetylamino)-1,3-thiazol-5-yl]methyl}piperidin-4-ylidene)methyl]-N-methylbenzamide To a solution of 4-([1-[(2-acetamido-1,3-thiazol-5-yl)methyl]piperidin-4-ylidene]methyl)benzoic acid (Example 27) (100 mg, 0.27 mmol) in dichloromethane (20 mL) was added methanamine hydrochloride (36.18 mg, 0.54 mmol), TEA (103.5 mg, 1.02 mmol), 1H-1,2,3-benzotriazol-1-ol (72.9 mg, 0.54 mmol), and EDC.HCl (109 mg, 0.57 mmol). The resulting solution was stirred overnight at ambient temperature. The residue was diluted with 50 mL of H$_2$O and the resulting solution was extracted with 3×50 mL of dichloromethane. The organic layers were combined and dried over anhydrous sodium sulfate and concentrated under vacuum. The residue was purified by preparative TLC (DCM/MeOH=15/1) to afford the title compound. (ES, m/z): [M+H]$^+$ 385; $^1$H NMR (300 MHz, CDCl$_3$) δ 10.68 (s, 1H), 7.92 (s, 2H), 7.23-7.19 (m, 2H) 6.26 (s, 1H), 6.06 (s, 1H), 3.69 (s, 2H), 3.00 (s, 3H), 2.62-2.39 (m, 8H), 2.33 (s, 3H).

Example 31

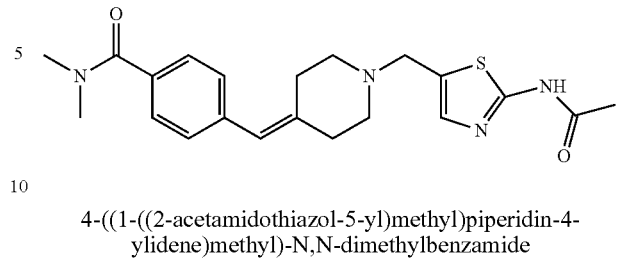

4-((1-((2-acetamidothiazol-5-yl)methyl)piperidin-4-ylidene)methyl)-N,N-dimethylbenzamide The title compound was prepared in an identical fashion to Example 30 from 4-([1-[(2-acetamido-1,3-thiazol-5-yl)methyl]piperidin-4-ylidene]methyl)benzoic acid (EXAMPLE 27). (ES, m/z): [M+H]$^+$ 399.

SCHEME B

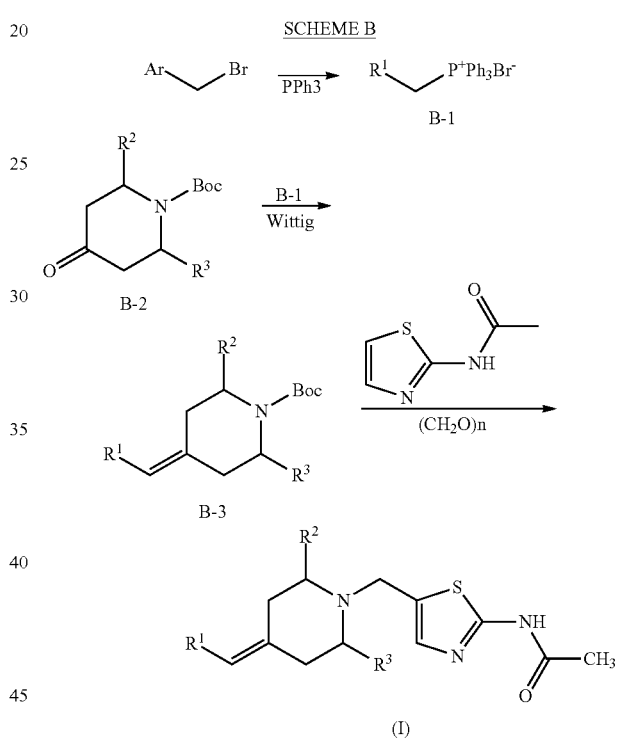

Compounds of the formula (I) may alternatively be prepared by the route shown in Scheme B from tert-butyl 4-oxopiperidine-1-carboxylate (B-2) via a Wittig reaction with the corresponding arylmethylene phosphonium bromide (B-1), which may be synthesized from the corresponding arylmethyl bromide. Removal of the BOC group under acidic conditions may be followed by iminium formation with paraformaldehyde, followed by nucleophilic addition of N-acylaminothiazole to afford compounds of the formula (I).

Example 32

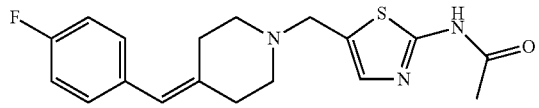 [SMILES: CC(=O)Nc1ncc(CN2CCC(=Cc3ccc(F)cc3)CC2)s1]

N-[5-({4-[(4-fluorophenyl)methylidene]piperidin-1-yl}methyl)-1,3-thiazol-2-yl]acetamide

Step 1: [(4-fluorophenyl)methyl]triphenylphosphanium chloride

To a solution of 1-(chloromethyl)-4-fluorobenzene (5 mL, 41.7 mmol) in toluene at 100° C. was added triphenylphosphine (5 g, 19.06 mmol). The mixture was stirred for 1 hour, then cooled and was precipitated by the addition of ether (50 ml). The solids were collected by filtration to give the title compound.

Step 2: Tert-butyl 4-(4-fluorobenzylidene)piperidine-1-carboxylate

To a solution of the intermediate from Step 1 (5 g, 12.29 mmol) in tetrahydrofuran (50 mL) was added butyllithium (4.5 mL of a 2.5 M solution) dropwise at 0° C. and stirred for 30 min at 10° C., then a solution of tert-butyl 4-oxopiperidine-1-carboxylate (2.5 g, 12.55 mmol) in tetrahydrofuran was added to the solution dropwise with stirring at 0° C. The resulting solution was stirred for 15 hours at 10° C. The reaction was quenched by slow addition to excess saturated aqueous NH$_4$Cl (20 mL). The resulting mixture was extracted with ethyl acetate (3×30 mL), and the organic layer was dried over anhydrous magnesium sulfate and concentrated under vacuum. The residue was applied onto a silica gel column with 3%-9% ethyl acetate in petroleum ether to give the title compound. (ES, m/z)[M+H]$^+$ 292.1; $^1$H NMR (300 MHz, CDCl$_3$), δ: 7.13-7.18 (m, 2H), 6.99-7.05 (m, 2H), 6.33 (s, 1H), 3.50-3.54 (m, 2H), 3.39-3.44 (m, 2H), 2.41-2.45 (m, 2H), 2.32-2.36 (m, 2H), 1.49 (s, 9H).

Step 3: 4-[(4-fluorophenyl)methylidene]piperidine

To a solution of the intermediate from Step 2 (2.5 g, 8.58 mmol) in methanol (10 mL) was added a saturated solution of hydrogen chloride in MeOH (5 mL) and the resulting solution was stirred for 3 h at 10° C. The solution was neutralized with saturated aqueous NaHCO$_3$. The resulting solution was extracted with ethyl acetate (30 mL×3), and the organic layer was dried over anhydrous magnesium sulfate and concentrated under vacuum. The residue was purified by a silica gel column with 5%-10% methanol in dichloromethane to give the title compound. (ES, m/z)[M+H]$^+$ 192.1; $^1$H NMR (300 MHz, CDCl$_3$), δ: 7.13-7.18 (m, 2H), 6.93-7.06 (m, 2H), 6.31 (s, 1H), 3.06-3.09 (m, 2H), 2.94-2.97 (m, 2H), 2.53-2.56 (m, 2H), 2.44-2.48 (m, 2H).

Step 4: N-[5-([4-[(4-fluorophenyl)methylidene]piperidin-1-yl]methyl)-1,3-thiazol-2-yl]acetamide To a solution of the intermediate prepared in Step 3 (1.3 g, 6.80 mmol) in AcOH (10 mL) was added formaldehyde (10 mL), N-(1,3-thiazol-2-yl)acetamide (1.5 g, 10.55 mmol) and the resulting solution was stirred overnight at 100° C. The resulting mixture was concentrated under vacuum. The residue was dissolved in tetrahydrofuran (50 mL), and the pH value of the solution was adjusted to 10 with saturated aqueous K$_2$CO$_3$. The solution was extracted with tetrahydrofuran (50 mL×3) and the organic layer was washed with brine (10 mL), dried over anhydrous magnesium sulfate and concentrated under vacuum. The residue was applied onto a silica gel column with 3% methanol in dichloromethane to give the title compound. (ES, m/z)[M+H]$^+$ 346.0; 1H NMR (300 MHz, CD$_3$OD), δ: 7.25 (s, 1H), 7.16-7.22 (m, 2H), 7.00-7.07 (m, 2H), 6.30 (s, 1H), 3.74 (s, 2H), 2.58-2.62 (m, 2H), 2.49 (s, 4H), 2.40-2.44 (m, 2H), 2.22 (s, 3H).

TABLE 3

The following compounds were prepared according to the general procedure provided in Scheme B, Example 32 and procedures herein. The starting materials are prepared as described herein, commercially available, or may be prepared from commercially available reagents using conventional reactions well known in the art.

| Ex. | Structure | Name | Mass [M + H] |
| --- | --- | --- | --- |
| 33 | 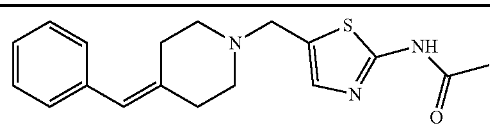 | N-(5-{[4-(phenylmethylidene)piperidin-1-yl]methyl}-1,3-thiazol-2-yl)acetamide | Calc'd 328, found 328 |
| 34 | 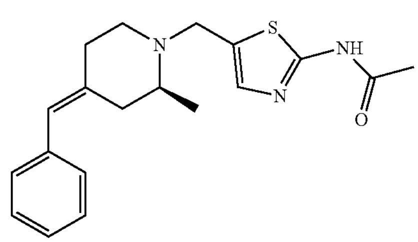 [SMILES: CC(=O)Nc1ncc(CN2CC/C(=C/c3ccccc3)C[C@@H]2C)s1] | (S,Z)-N-(5-{(4-benzylidene-2-methylpiperidin-1-yl)methyl)thiazol-2-yl)acetamide | Calc'd 342, found 342 |
| 35 | 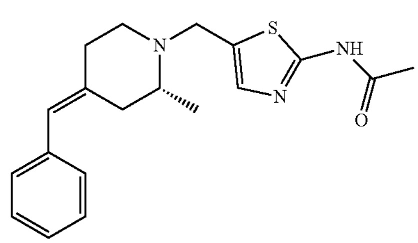 [SMILES: CC(=O)Nc1ncc(CN2CC/C(=C/c3ccccc3)C[C@H]2C)s1] | (R,Z)-N-(5-((4-benzylidene-2-methylpiperidin-1-yl)methyl)thiazol-2-yl)acetamide | Calc'd 342, found 342 |

TABLE 3-continued

The following compounds were prepared according to the general procedure provided in Scheme B, Example 32 and procedures herein. The starting materials are prepared as described herein, commercially available, or may be prepared from commercially available reagents using conventional reactions well known in the art.

| Ex. | Structure | Name | Mass [M + H] |
|---|---|---|---|
| 36 | 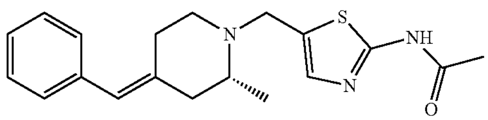 [SMILES: CC(=O)Nc1ncc(CN2CC/C(=C\c3ccccc3)C[C@H]2C)s1] | (R,E)-N-(5-((4-benzylidene-2-methylpiperidin-1-yl)methyl)thiazol-2-yl)acetamide | Calc'd 342, found 342 |
| 37 | 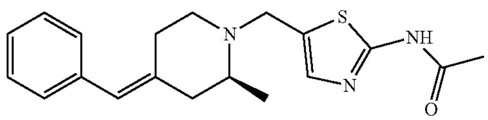 [SMILES: CC(=O)Nc1ncc(CN2CC/C(=C\c3ccccc3)C[C@@H]2C)s1] | (S,E)-N-(5-((4-benzylidene-2-methylpiperidin-1-yl)methyl)thiazol-2-yl)acetamide | Calc'd 342, found 342 |
| 38 | 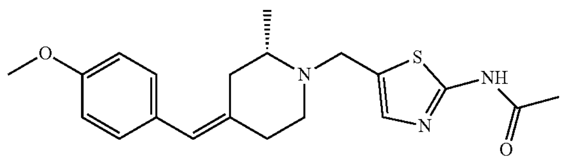 [SMILES: COc1ccc(/C=C2/CCN(Cc3cnc(NC(C)=O)s3)[C@@H](C)C2)cc1] | (S,Z)-N-(5-((4-(4-methoxybenzylidene)-2-methylpiperidin-1-yl)methyl)thiazol-2-yl)acetamide | Calc'd 372, found 372 |
| 39 | 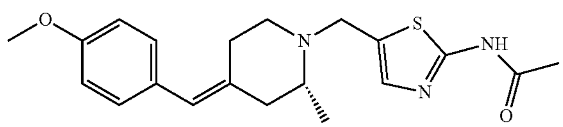 [SMILES: COc1ccc(/C=C2\CCN(Cc3cnc(NC(C)=O)s3)[C@H](C)C2)cc1] | (R,E)-N-(5-((4-(4-methoxybenzylidene)-2-methylpiperidin-1-yl)methyl)thiazol-2-yl)acetamide | Calc'd 372, found 372 |
| 40 | 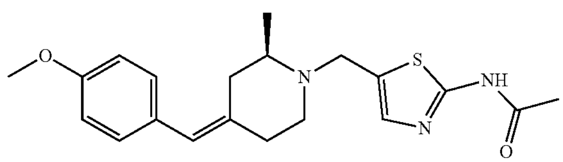 [SMILES: COc1ccc(/C=C2/CCN(Cc3cnc(NC(C)=O)s3)[C@H](C)C2)cc1] | (R,Z)-N-(5-((4-(4-methoxybenzylidene)-2-methylpiperidin-1-yl)methyl)thiazol-2-yl)acetamide | Calc'd 372, found 372 |
| 41 | 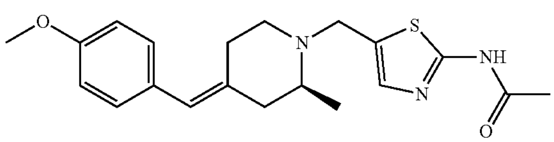 [SMILES: COc1ccc(/C=C2\CCN(Cc3cnc(NC(C)=O)s3)[C@@H](C)C2)cc1] | (S,E)-N-(5-((4-(4-methoxybenzylidene)-2-methylpiperidin-1-yl)methyl)thiazol-2-yl)acetamide | Calc'd 372, found 372 |

SCHEME C

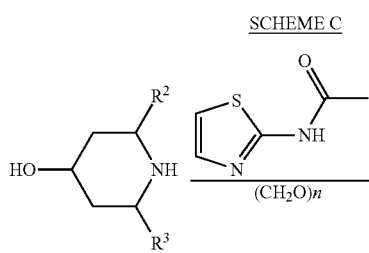
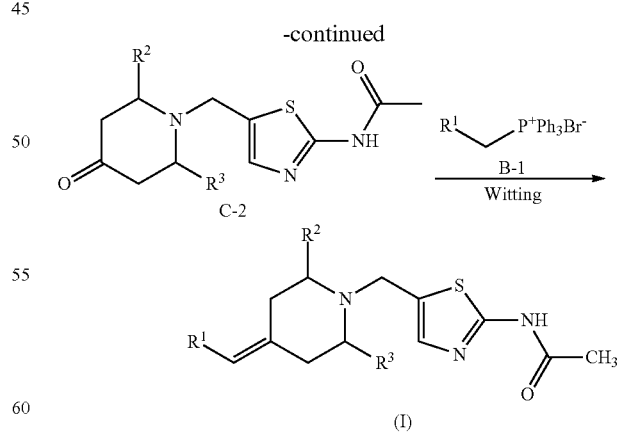

Compounds of the formula (I) may alternatively be prepared via the route shown in Scheme C from 4-hydroxy piperidine by iminium formation with paraformaldehyde, followed by nucleophilic addition of N-acylaminothiazole to afford the substituted piperidine (C-1). This intermediate may be oxidized to the corresponding ketone using a Swern oxidation or other methods know to those skilled in the art to afford the piperidone intermediate (C-2). Separately, the corresponding aryl methylene phosphonium ylide (B-1) may be prepared from the appropriate bromide. Coupling of C-2 and B-1 via a Wittig reaction affords compounds of the general structure (I).

Example 42

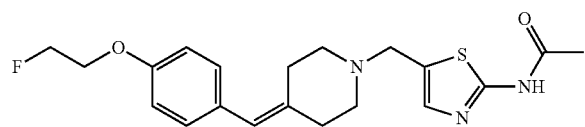 [SMILES: CC(=O)Nc1ncc(CN2CCC(=Cc3ccc(OCCF)cc3)CC2)s1]

N-{5-[(4-{[4-(2-fluoroethoxy)phenyl]
methylidene}piperidin-1-yl)methyl]-1,3-thiazol-2-
yl}acetamide Step 1: N-[5-[(4-hydroxypiperidin-1-yl)methyl]-1,3-
thiazol-2-yl]acetamide (8-2)

To a solution of N-(thiazol-2-yl)acetamide (30 g, 211 mmol) and piperidin-4-ol (25.6 g, 253 mmol) in acetic acid (200 mL) was added paraformaldehyde (31.6 g, 1 mol) in several batches at 100° C. After stirring overnight at 100° C., volatiles were removed under vacuum to give a residue, which was dissolved into THF (300 mL), neutralized with saturated aqueous potassium carbonate and washed with brine (3×30 mL). The organic layer was dried over anhydrous sodium sulfate and concentrated under vacuum to give 1-((2-acetamidothiazol-5-yl)methyl)piperidin-4-yl acetate. The crude oil was dissolved into methanol (500 mL) and treated with potassium carbonate (15 g, 100 mmol) for 12 hours at room temperature, then filtered through a short silica gel column. Solvent was distilled out to give the crude product, which was purified by a silica gel column, eluted with 2%-3% methanol in dichloromethane to give the title compound; (ES, m/z): [M+H]-256.1; $^1$H NMR (300 MHz, CD$_3$OD) δ 7.26 (s, 1H), 3.72 (s, 2H), 3.67-3.55 (m, 1H), 2.86-2.81 (m, 2H), 2.28-2.24 (m, 2H), 2.12 (s, 3H), 2.08-2.07 (m, 2H), 1.64-1.57 (m, 2H).

Step 2: N-[5-[(4-oxopiperidin-1-yl)methyl]-1,3-
thiazol-2-yl]acetamide

To a solution of N-[5-[(4-hydroxypiperidin-1-yl)methyl]-1,3-thiazol-2-yl]acetamide (Step 1) (1.03 g, 4 mmol) in dichloromethane (30 mL) was added DMP (3.1 g, 7 mmol) at room temperature. After additional 4 hours at room temperature, the reaction was quenched by the addition of saturated sodium bicarbonate aqueous solution (10 mL). The aqueous layer was extracted with dichloromethane (3×100 mL). The combined organic solution was washed with brine (50 mL), dried over anhydrous sodium sulfate, filtered and concentrated. The crude residue was purified by a silica gel column, eluted with 1%-3% methanol in dichloromethane to afford the title compound; (ES, m/z): [M+H]$^+$ 254.0; $^1$H NMR (300 MHz, CDCl$_3$) δ 11.68 (br, 1H), 7.25 (s, 1H), 4.30 (s, 2H), 2.82 (t, J=6.0 Hz, 4H), 2.49 (t, J=6.0 Hz, 4H), 2.34 (s, 3H).

Step 3: 4-(2-fluoroethoxy)benzaldehyde

A solution of 4-hydroxybenzaldehyde (5 g, 41 mmol), 2-fluoroethan-1-ol (7.8 g, 122 mmol) and triphenylphosphane (53.7 g, 205 mmol) in THF (50 mL) was treated with diethyl azodicarboxylate (42.8 g, 246 mmol) for 2 hours at room temperature. The reaction was then quenched by water (150 mL) and extracted with ethyl acetate (3×50 mL). The combined organic layer was washed with brine (2×30 mL), dried over anhydrous sodium sulfate and concentrated under vacuum to give a residue, which was purified by a silica gel column, eluted with 1%-5% ethyl acetate in petroleum ether to give the title compound; $^1$H NMR (300 MHz, CDCl$_3$) δ 8.10 (s, 1H), 7.49 (d, J=8.4 Hz, 2H), 7.21 (d, J=8.7 Hz, 2H), 4.79 (td, J$_1$=4.2 Hz, J$_2$=47.1 Hz, 2H), 4.24 (td, J$_1$=4.2 Hz, J$_2$=27.9 Hz, 2H).

Step 4: [4-(2-fluoroethoxy)phenyl]methanol

To a solution of 4-(2-fluoroethoxy)benzaldehyde (Step 3) (5.2 g, 31 mmol) in methanol (30 mL) was added NaBH$_4$ (2.4 g, 64 mmol) and stirred overnight at 25° C. The resulting solution was quenched with water (2 mL) and concentrated under vacuum to give a residue, which was purified by a silica gel column, eluted with 10% ethyl acetate in petroleum ether to give the title compound; (ES, m/z): [M+H]$^+$ 171.0; $^1$H NMR (300 MHz, CDCl$_3$) δ 7.29 (d, J=8.4 Hz, 2H), 6.93 (d, J=8.7 Hz, 2H), 4.77 (td, J$_1$=4.2 Hz, J$_2$=47.1 Hz, 2H), 4.68 (s, 2H), 4.23 (td, J$_1$=4.2 Hz, J$_2$=27.9 Hz, 2H).

Step 5: 1-(bromomethyl)-4-(2-fluoroethoxy)benzene

To a solution of [4-(2-fluoroethoxy)phenyl]methanol (Step 4) (4 g, 23 mmol) in dichloromethane (50 mL) was added PPh$_3$ (7.3 g, 28 mmol) and CBr$_4$ (9.2 g, 28 mmol) and stirred for 12 hours at 25° C. The reaction was then quenched with water (50 mL). The organic layer was separated, dried over anhydrous sodium sulfate and concentrated under vacuum to give a residue, which was purified by a silica gel column, eluted with 1%-5% ethyl acetate in petroleum ether to give the title compound: $^1$H NMR (300 MHz, CDCl$_3$) δ 7.33 (d, J=8.4 Hz, 2H), 6.89 (d, J=8.7 Hz, 2H), 4.75 (td, J$_1$=4.2 Hz, J$_1$=44.4 Hz, 2H), 4.49 (s, 2H), 4.21 (td, J$_1$=4.2 Hz, J$_2$=20.4 Hz, 2H).

Step 6:
(4-(2-fluoroethoxy)benzyl)triphenylphosphonium
bromide

To a solution of -(bromomethyl)-4-(2-fluoroethoxy)benzene (Step 5) (3.4 g, 14.6 mmol) in toluene (30 mL) was added triphenylphosphane (7.8 g, 30 mmol) and stirred for 1 h at 110° C. After cooled to room temperature, solids were collected by filtration and washed with ether (2×30 mL) to give the title compound; $^1$H NMR (400 MHz, CD$_3$OD) δ 7.89-7.75 (m, 9H), 7.71-7.64 (m, 6H), 7.05 (d, J=6.3 Hz, 2H), 6.69 (d, J=8.4 Hz, 2H), 5.36 (d, J=13.8 Hz, 2H), 4.73 (td, J$_1$=3.9 Hz, J$_2$=47.1 Hz, 2H), 4.13 (td, J$_1$=3.9 Hz, J$_2$=24 Hz, 2H).

Step 7: N-(5-((4-(4-(2-fluoroethoxy)benzylidene)
piperidin-1-yl)methyl)thiazol-2-yl)acetamide A suspension of (4-(2-fluoroethoxy)benzyl)triphenylphosphonium bromide (5.3 g, 11.7 mmol) in THF (50 mL) was treated with 1 N solution of LiHMDS (34 mL, 34 mmol) in THF at −20° C. for 10 min, followed by the addition of N-[5-[(4-oxopiperidin-1-yl)methyl]-1,3-thiazol-2-yl]acetamide (Step 6) (1.5 g, 5.9 mmol). The resulting solution was stirred for 12 hours at 50° C., then quenched with saturated aqueous NH$_4$Cl solution (100 ml) and extracted with ethyl acetate (3×200 mL). The combined organic layer was washed with brine (2×30 mL), dried over anhydrous magnesium sulfate and concentrated under vacuum to give a residue, which was purified by a silica gel column, eluted with 1%-5% methanol in dichloromethane to give the title compound; (ES, m/z): [M+H]⁺ 370.0; ¹H NMR (300 MHz, CD₃OD) δ 7.26 (s, 1H), 7.12 (d, J=8.7 Hz, 2H), 6.90 (d, J=8.7 Hz, 2H), 6.27 (s, 1H), 4.70 (td, $J_1$=4.2 Hz, $J_2$=47.1 Hz, 2H), 4.21 (td, $J_1$=4.2 Hz, $J_2$=28.8 Hz, 2H), 3.73 (s, 2H), 2.61-2.41 (m, 8H), 2.21 (s, 3H).

TABLE 4

The following compounds were prepared according to the general procedure provided in Scheme C, Example 38 and procedures herein. The starting materials are prepared as described herein, commercially available, or may be prepared from commercially available reagents using conventional reactions well known in the art.

| Ex. | Structure | Name | Mass [M + H] |
|---|---|---|---|
| 43 | 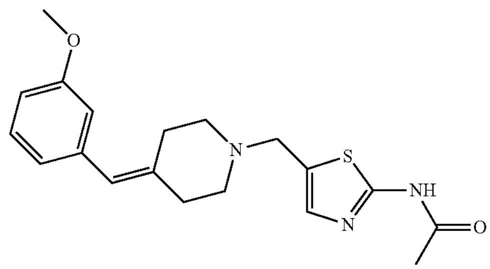 [SMILES: COc1cccc(C=C2CCN(Cc3cnc(NC(C)=O)s3)CC2)c1] | N-(5-((4-(3-methoxybenzylidene)piperidin-1-yl)methyl)thiazol-2-yl)acetamide | Calc'd 358, found 358 |
| 44 | 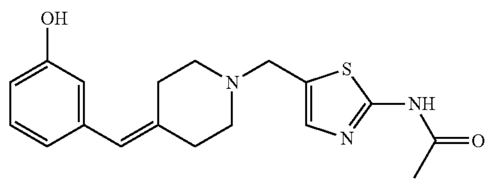 [SMILES: CC(=O)Nc1ncc(CN2CCC(=Cc3cccc(O)c3)CC2)s1] | N-(5-((4-(3-hydroxybenzylidene)piperidin-1-yl)methyl)thiazol-2-yl)acetamide | Calc'd 344, found 344 |
| 45 | 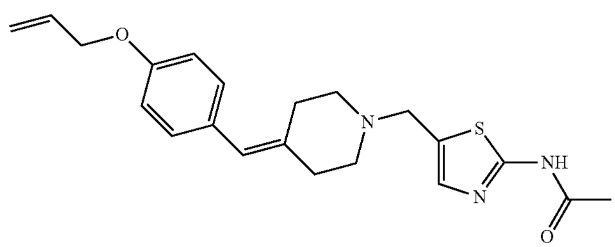 [SMILES: C=CCOc1ccc(C=C2CCN(Cc3cnc(NC(C)=O)s3)CC2)cc1] | N-{5-[(4-{[4-(prop-2-en-1-yloxy)phenyl]methylidene}piperidin-1-yl)methyl]-1,3-thiazol-2-yl}acetamide | Calc'd 384, found 384 |
| 46 | 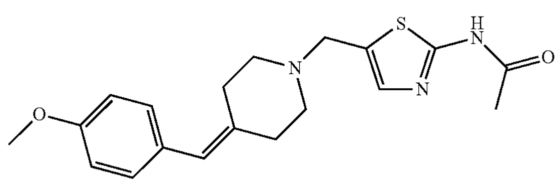 [SMILES: COc1ccc(C=C2CCN(Cc3cnc(NC(C)=O)s3)CC2)cc1] | N-[5-({4-[(4-methoxyphenyl)methylidene]piperidin-1-yl}methyl)-1,3-thiazol-2-yl]acetamide | Calc'd 358, found 358 |
| 47 | 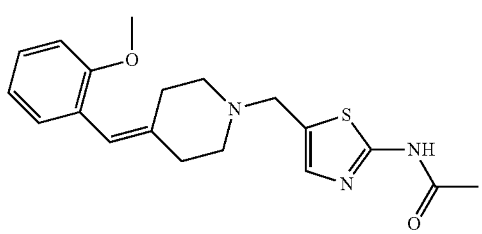 [SMILES: COc1ccccc1C=C1CCN(Cc2cnc(NC(C)=O)s2)CC1] | N-(5-((4-(2-methoxybenzylidene)piperidin-1-yl)methyl)thiazol-2-yl)acetamide | Calc'd 358, found 358 |
| 48 | 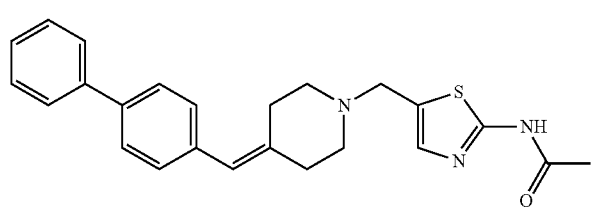 [SMILES: CC(=O)Nc1ncc(CN2CCC(=Cc3ccc(-c4ccccc4)cc3)CC2)s1] | N-(5-((4-([1,1'-biphenyl]-4-ylmethylene)piperidin-1-yl)methyl)thiazol-2-yl)acetamide | Calc'd 404, found 404 |

SCHEME D

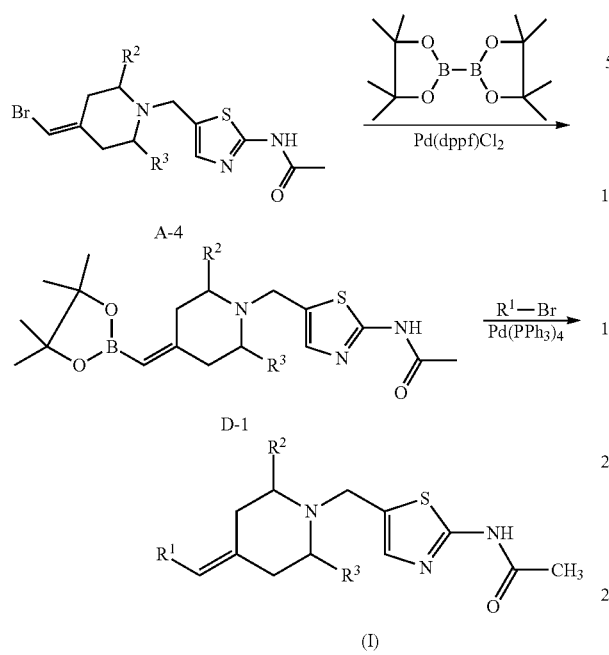

Compounds of the formula (I) may alternatively be prepared via the route from intermediate A-4 shown in Scheme D. This intermediate may be borylated using bis(pinacolato)diboron and an appropriate palladium catalyst such as [1,1'-bis(diphenylphosphino)ferrocene]palladium(II) dichloride to give the vinylic borylpiperidine (D-1). This intermediate may be coupled to an appropriate aryl or heteroaryl bromide via the Suzuki reaction to afford compounds of the general structure (I).

Example 49

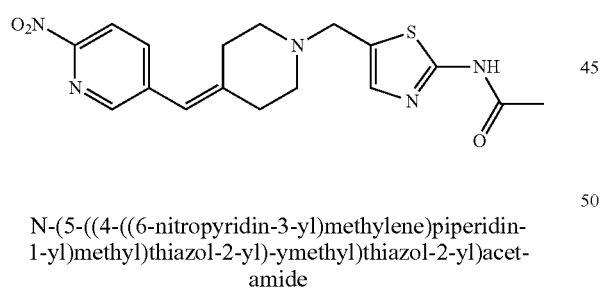

N-(5-((4-((6-nitropyridin-3-yl)methylene)piperidin-1-yl)methyl)thiazol-2-yl)-ymethyl)thiazol-2-yl)acetamide In a nitrogen atmosphere, a mixture of N-(5-((4-(bromomethylene)piperidin-1-yl)methyl)thiazol-2-yl)acetamide (A-4) (800 mg, 2.4 mmol), bis(pinacolato)diboron (731 mg, 2.9 mmol), Pd(dppf)Cl₂ (352 mg, 0.5 mmol), PPh₃ (252 mg, 0.9 mmol) and KOAc (948 mg, 9.7 mmol) in DMF (30 mL) was kept at 80° C. for 3 hours. The resulting solution was cooled to room temperature followed by the addition of 5-bromo-2-nitropyridine (1.28 g, 6.3 mmol), Pd(PPh₃)₄ (240 mg, 0.2 mmol), potassium carbonate (1.16 g, 8.4 mmol) and water (2 mL). After an additional 2 hours at 80° C., the resulting solution was quenched with water (150 mL) and extracted with dichloromethane (3×30 mL). The combined organic layers were washed with brine (3×30 mL), dried over anhydrous sodium sulfate and concentrated under vacuum to give a residue, which was purified by a silica gel column, eluted with 1%-3% methanol in dichloromethane to give the title compound; (ES, m/z): [M+H]⁺ 374.0; ¹H NMR (300 MHz, CD₃OD) δ 8.44 (s, 1H), 8.28 (d, J=8.4 Hz, 1H), 8.01 (d, J=8.1 Hz, 1H), 7.25 (s, 1H), 6.43 (s, 1H), 3.57 (s, 2H), 2.52-2.65 (m, 8H), 2.21 (s, 3H).

SCHEME E

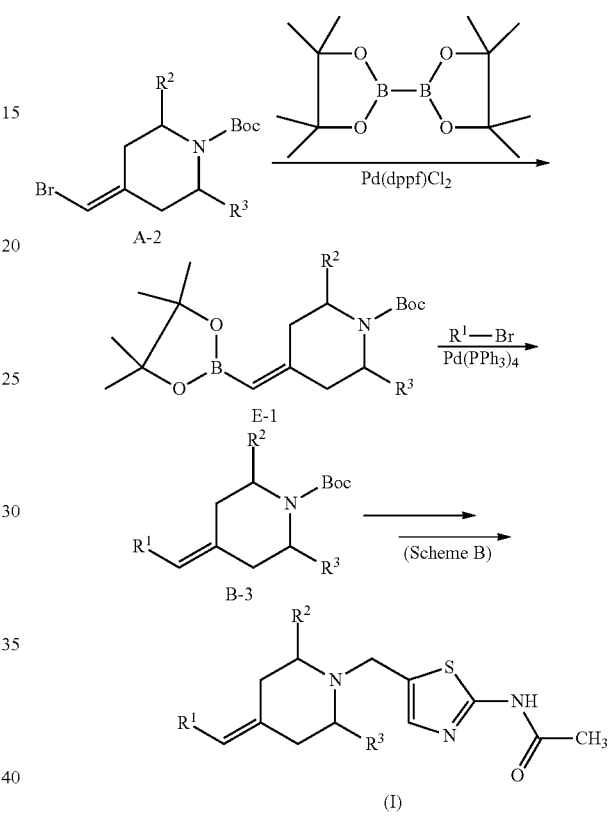

Example 50

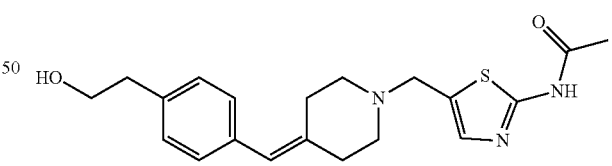

N-(5-((4-(4-(2-hydroxyethyl)benzylidene)piperidin-1-yl)methyl)thiazol-2-yl)acetamide Step 1: tert-butyl 4-[(tetramethyl-1,3,2-dioxaborolan-2-yl)methylidene]piperidine-1-carboxylate To a solution of tert-butyl 4-(bromomethylidene)piperidine-1-carboxylate (2 g, 7.24 mmol) in N,N-dimethylformamide (80 mL) was added 4,4,5,5-tetramethyl-2-(tetramethyl-1,3,2-dioxaborolan-2-yl)-1,3,2-dioxaborolane (3.71 g, 14.61 mmol), KOAc (2.86 g, 29.14 mmol), and Pd(dppf)Cl₂

(590 mg, 0.81 mmol). The resulting solution was stirred for 4 h at 80° C. The resulting mixture was concentrated under vacuum, affording the title compound which was used directly in Step 2.

Step 2: Tert-butyl 4-[[4-(2-hydroxyethyl)phenyl]methylidene]piperidine-1-carboxylate To a solution of tert-butyl 4-[(tetramethyl-1,3,2-dioxaborolan-2-yl)methylidene]piperidine-1-carboxylate (Step 1) (1.6 g, 4.95 mmol) in N,N-dimethylformamide (80 mL), 2-(4-bromophenyl)ethan-1-ol (1.48 g, 7.36 mmol), potassium carbonate (1.35 g, 9.77 mmol), Pd(PPh$_3$)$_4$ (560 mg, 0.48 mmol) was added. The resulting solution was stirred for 3 h at 80° C. The reaction was then quenched by the addition of water. The resulting solution was extracted with of ethyl acetate and the organic layers combined and dried over anhydrous sodium sulfate. The residue was applied onto a silica gel column with ethyl acetate/petroleum ether (1:80~1:1), affording the title compound.

Step 3: 2-[4-(piperidin-4-ylidenemethyl)phenyl]ethan-1-ol

To a solution of tert-butyl 4-[[4-(2-hydroxyethyl)phenyl]methylidene]piperidine-1-carboxylate (Step 2) (1.5 g, 4.73 mmol) in dichloromethane (20 mL) was added trifluoroacetic acid (2 mL, 2.30 mmol). The resulting solution was stirred for 3 h at room temperature. The resulting mixture was concentrated under vacuum, affording the title compound.

Step 4: 2-[4-([1-[(2-acetamido-1,3-thiazol-5-yl)methyl]piperidin-4-ylidene]methyl)phenyl]ethyl acetate To a solution of 2-[4-(piperidin-4-ylidenemethyl)phenyl]ethan-1-ol (Step 3) (800 mg, 3.68 mmol) in acetic acid (20 mL), was added N-(1,3-thiazol-2-yl)acetamide (530 mg, 3.73 mmol) and methanol (450 mg, 14.04 mmol). The resulting solution was stirred overnight at 100° C. The reaction was then quenched by the addition of saturated aqueous K$_2$CO$_3$ and the pH value of the solution was adjusted to 7~8. The resulting solution was extracted with ethyl acetate and the organic layers combined and dried over anhydrous sodium sulfate and concentrated under vacuum. The residue was applied onto a silica gel column with dichloromethane/methanol (80-10:1) affording the title compound.

Step 5: N-[5-[(4-[[4-(2-hydroxyethyl)phenyl]methylidene]piperidin-1 1-yl)methyl]-1,3-thiazol-2-yl]acetamide To a solution of 2-[4-([1-[(2-acetamido-1,3-thiazol-5-yl)methyl]piperidin-4-ylidene]methyl)phenyl]ethyl acetate (Step 4) (220 mg, 0.53 mmol) in methanol (25 mL) was added potassium carbonate (7.3 mg, 0.05 mmol). The resulting solution was stirred for 3 h at room temperature. The reaction was then quenched by the addition of acetic acid. The resulting mixture was concentrated under vacuum. The residue was applied onto a silica gel column with dichloromethane/methanol (80-20:1), affording the title compound; (ES, m/z): [M+H]$^+$ 372.3; $^1$H NMR (300 MHz, CDCl$_3$) δ 11.1 (s, 1H), 7.32-7.11 (m, 5H) 6.26 (s, 1H), 3.86 (m, 2H), 3.74 (s, 2H), 2.85 (t, J=6.6 Hz, 2H), 2.67-2.34 (m, 8H), 2.30 (s, 3H), 1.50 (m, 2H).

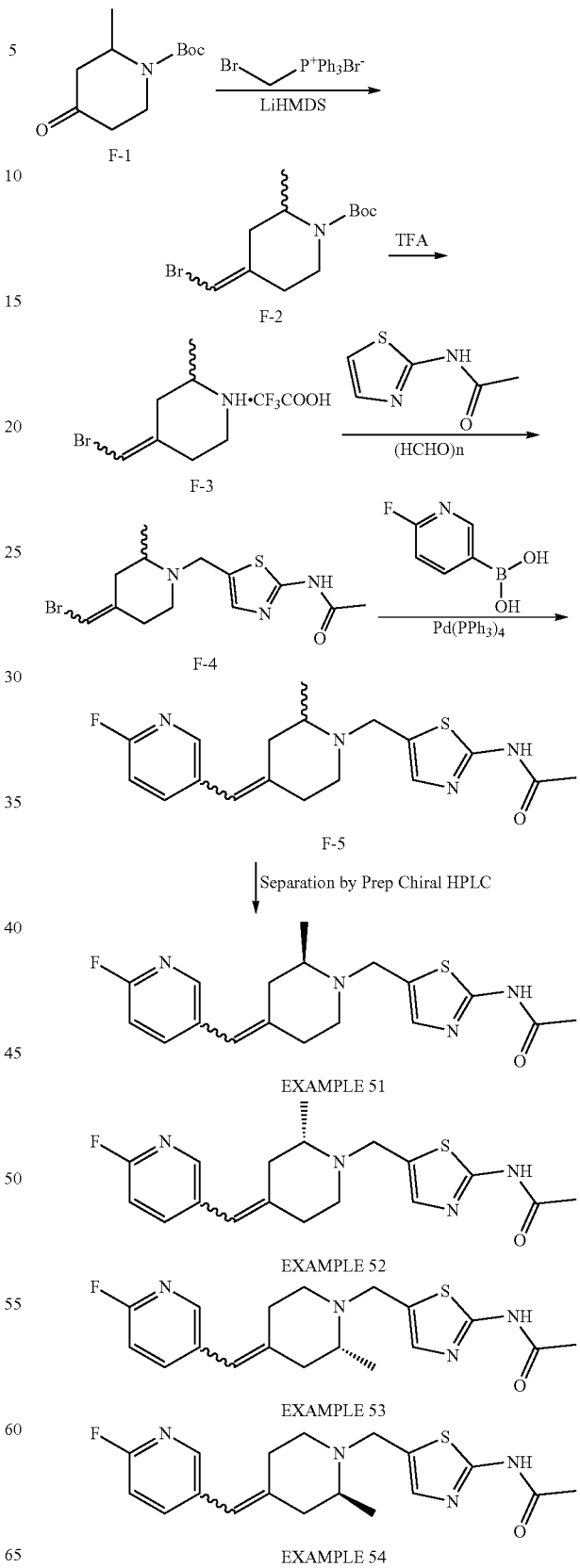

SCHEME F

Example 51: (R,Z)—N-(5-((4-((6-fluoropyridin-3-yl)methylene)-2-methylpiperidin-1-yl)methyl)thiazol-2-yl)acetamide Example 52: (S,Z)—N-(5-((4-((6-fluoropyridin-3-yl)methylene)-2-methylpiperidin-1-yl)methyl)thiazol-2-yl)acetamide Example 53: (R,E)-N-(5-((4-((6-fluoropyridin-3-yl)methylene)-2-methylpiperidin-1-yl)methyl)thiazol-2-yl)acetamide and Example 54: (S,E)-N-(5-((4-((6-fluoropyridin-3-yl)methylene)-2-methylpiperidin-1-yl)methyl)thiazol-2-yl)acetamide

Step 1: tert-butyl 4-(bromomethylene)-2-methylpiperidine-1-carboxylate (F-2)

A suspension of (bromomethyl) triphenylphosphonium bromide (40 g, 91.7 mmol) in THF (500 mL) was treated with 1 N solution of LiHMDS (201 mL, 201 mmol) in THF for 30 min at −20° C., followed by the addition of tert-butyl 2-methyl-4-oxopiperidine-1-carboxylate (F-1) (10 g, 46.9 mmol). After additional 1.5 hours at room temperature, the reaction was quenched with saturated aqueous ammonium chloride solution (500 mL). The resulting solution was extracted with ethyl acetate (3×200 mL). The combined organic layer was washed with brine (3×50 mL), dried over anhydrous sodium sulfate and concentrated under vacuum to give a residue, which was purified by a silica gel column, eluted with 10%-20% ethyl acetate in petroleum ether to give the title compound as an oil (5 g); (ES, m/z) [M+H]$^+$ 290.0, 292.0; $^1$H NMR (300 MHz, CDCl$_3$) δ 6.12 (s, 0.5H), 5.96 (s, 0.5H), 4.60 (br s, 0.5H), 4.44 (br s, 0.5H), 4.05-4.02 (m, 1H), 2.92-2.88 (m, 1H), 2.76-2.69 (m, 1H), 2.43-2.06 (m, 3H), 1.48 (s, 9H), 1.16 (d, J=6.3 Hz, 3H).

Step 2: N-(5-((4-(bromomethylene)-2-methylpiperidin-1-yl)methyl)thiazol-2-yl)acetamide (F-4)

To a solution of tert-butyl 4-(bromomethylene)-2-methylpiperidine-1-carboxylate (F-2) (480 mg, 1.65 mmol) in dichloromethane (12 mL) was added trifluoroacetic acid (4 mL) at room temperature. After 2 hours, volatiles were distilled out to give a residue, which was dissolved into acetic acid (20 mL), followed by the addition of N-(1,3-thiazol-2-yl)acetamide (270 mg, 1.9 mmol) and paraformaldehyde (165 mg, 5.5 mmol). The resulting solution was stirred overnight at 100° C., then cooled to room temperature and concentrated under vacuum. The crude residue was dissolved into dichloromethane (20 mL), diluted with water (20 mL) and neutralized with sodium bicarbonate. The organic layer was separated and the aqueous layer was extracted with dichloromethane (3×20 mL). The combined organic layer was dried over anhydrous magnesium sulfate and concentrated to give a residue, which was purified by a silica gel column, eluted with 1%-2% methanol in dichloromethane to the title compound as a solid (210 mg); (ES, m/z) [M+H]$^+$ 344.0, 346.0; $^1$H NMR (300 MHz, CDCl$_3$) δ 7.21 (s, 1H), 5.93 (s, 1H), 4.00-3.72 (m, 2H), 2.92-2.82 (m, 1H), 2.76-2.45 (m, 4H), 2.30 (s, 3H), 2.19-2.09 (m, 3H), 1.19-1.16 (m, 3H).

Step 3: N-(5-((4-((6-fluoropyridin-3-yl)methylene)-2-methylpiperidin-1-yl)methyl)thiazol-2-yl)acetamide (F-5)

To a solution of N-(5-((4-(bromomethylene)-2-methylpiperidin-1-yl)methyl)thiazol-2-yl)acetamide (F-4) (450 mg, 1.3 mmol) in DMF (30 mL) was added (6-fluoropyridin-3-yl)boronic acid (276 mg, 2.0 mmol), potassium carbonate (360 mg, 2.6 mmol), Pd(PPh$_3$)$_4$ (75 mg, 0.06 mmol) and water (5 mL). The resulting solution was stirred for 1 hour at 80° C. under nitrogen atmosphere. After that, the reaction was cooled to room temperature and quenched diluted with saturated aqueous ammonium chloride solution (100 mL). The resulting solution was extracted with dichloromethane (3×50 mL) and the combined organic layer was washed with brine (2×50 mL), dried over anhydrous magnesium sulfate and concentrated. The crude residue was purified by a silica gel column, eluted with 1%-3% methanol in dichloromethane to give a mixture of the four isomers of N-(5-((4-((6-fluoropyridin-3-yl)methylene)-2-methylpiperidin-1-yl)methyl)thiazol-2-yl)acetamide (F-5) as a solid (200 mg), which was further separated by Prep-Chiral-HPLC with the following conditions: (Chiralpak IA, 0.46*25 cm, 5 um; Mobile phase: Hex:EtOH=70:30, flow rate: 1.0 ml/min, Total Run Time (min): 30; Temperature: 25° C.; Detector: 254 nm) to give:

Example 51

(R,Z)—N-(5-((4-((6-fluoropyridin-3-yl)methylene)-2-methylpiperidin-1-yl)methyl)thiazol-2-yl)acetamide (10.4 mg). (ES, m/z) [M+H]$^+$ 361.1; $^1$H NMR (300 MHz, CD$_3$OD): δ 8.00 (s, 1H), 7.76 (td, J=2.1 Hz, J$_2$=4.5 Hz, 1H), 7.25 (s, 1H), 7.02 (dd, J$_1$=2.4 Hz, J$_2$=8.4 Hz, 1H), 6.29 (s, 1H), 4.04 (d, J=14.4 Hz, 1H), 3.83 (d, J=14.4 Hz, 1H), 2.96-2.93 (m, 1H), 2.62-2.61 (m, 1H), 2.56-2.53 (m, 1H), 2.45-2.37 (m, 3H), 2.21 (s, 3H), 2.20-2.12 (m, 1H), 1.16 (d, 0.1=6.3 Hz, 3H); and

Example 52

(S,Z)—N-(5-((4-((6-fluoropyridin-3-yl)methylene)-2-methylpiperidin-1-yl)methyl)thiazol-2-yl)acetamide (9.4 mg); (ES, m/z) [M+H]$^+$ 361.1; $^1$H NMR (300 MHz, CD$_3$OD) δ 8.00 (s, 1H), 7.76 (td, J=2.1 Hz, d, =4.5 Hz, 1H), 7.25 (s, 1H), 7.02 (dd, J$_1$=2.4 Hz, J$_2$=8.4 Hz, 1H), 6.29 (s, 1H), 4.04 (d, J=14.4 Hz, 1H), 3.83 (d, J=14.4 Hz, 1H), 2.96-2.93 (m, 1H), 2.62-2.61 (m, 1H), 2.56-2.53 (m, 1H), 2.45-2.37 (m, 3H), 2.21 (s, 3H), 2.20-2.12 (m, 1H), 1.16 (d, J=6.3 Hz, 3H); and

Example 53

(R,E)-N-(5-((4-((6-fluoropyridin-3-yl)methylene)-2-methylpiperidin-1-yl)methyl)thiazol-2-yl)acetamide (9.6 mg); (ES, m/z) [M+H]$^+$ 361.1; $^1$H NMR (300 MHz, CD$_3$OD) δ 8.01 (s, 1H), 7.76 (td, J$_1$=2.1 Hz, J$_2$=4.5 Hz, 1H), 7.25 (s, 1H), 7.02 (dd, J$_1$=2.4 Hz, 12=8.4 Hz, 1H), 6.25 (s, 1H), 4.03 (d, J=14.4 Hz, 1H), 3.83 (d, J=14.4 Hz, 1H), 2.89-2.85 (m, 1H), 2.66-2.21 (m, 9H), 1.24 (d, J=6.3 Hz, 3H); and

Example 54

(S,E)-N-(5-((4-((6-fluoropyridin-3-yl)methylene)-2-methylpiperidin-1-yl)methyl)thiazol-2-yl)acetamide (10.4 mg); (ES, m/z) [M+H]$^+$ 361.1; $^1$H NMR (300 MHz, CD$_3$OD) δ 8.01 (s, 1H), 7.76 (td, J$_1$=2.1 Hz, J$_2$=4.5 Hz, 1H), 7.25 (s, 1H), 7.02 (dd, J$_1$=2.4 Hz, J$_2$=8.4 Hz, 1H), 6.25 (s, 1H), 4.03 (d, J=14.4 Hz, 1H), 3.83 (d, J=14.4 Hz, 1H), 2.89-2.85 (m, 1H), 2.66-2.21 (m, 9H), 1.24 (d, J=6.3 Hz, 3H).

TABLE 5

| Example | hOGA Ki (nM) |
|---|---|
| 1 | 0.3921 |
| 2 | 2.081 |
| 3 | 1.086 |
| 4 | 0.8605 |
| 5 | 3.526 |
| 6 | 0.6353 |
| 7 | 0.6896 |
| 8 | 0.387 |
| 9 | 0.2937 |
| 10 | 0.6143 |
| 11 | 3.155 |
| 12 | 0.7033 |
| 13 | 0.7413 |
| 14 | 1.449 |
| 15 | 3.374 |
| 16 | 3.404 |
| 17 | 0.09543 |
| 18 | 0.4268 |
| 19 | 1.035 |
| 20 | 1.792 |
| 21 | 0.2678 |
| 22 | 0.6343 |
| 23 | 1.514 |
| 24 | 1.366 |
| 26 | 0.1666 |
| 26 | 0.07527 |
| 27 | 0.4111 |
| 28 | 5.707 |
| 29 | 0.3236 |
| 30 | 0.43 |
| 31 | 0.1166 |
| 32 | 2.698 |
| 33 | 1.747 |
| 34 | 1.041 |
| 35 | 56.57 |
| 36 | 412 |
| 37 | 29.78 |
| 38 | 0.2868 |
| 39 | 125.8 |
| 40 | 71.18 |
| 41 | 9.611 |
| 42 | 0.625 |
| 43 | 2.93 |
| 44 | 1.128 |
| 45 | 6.114 |
| 46 | 1.996 |
| 47 | 2.452 |
| 48 | 53.81 |
| 49 | 1.597 |
| 50 | 0.241 |
| 51 | 218 |
| 52 | 0.3885 |
| 53 | 123 |
| 54 | 11.82 |

Assay for Determination of $K_I$ Values for Inhibition of O-GlcNAcase Activity

Experimental procedure for kinetic analyses: Enzymatic reactions were carried out in a reaction containing 50 mM $NaH_2PO_4$, 100 mM NaCl and 0.1% BSA (pH 7.0) using 2 mM 4-Methylumbelliferyl N-acetyl-β-D-glucosaminide dihydrate (Sigma M2133) dissolved in dd$H_2O$, as a substrate. The amount of purified human O-GlcNAcase enzyme used in the reaction was 0.7 nM. Test compound of varying concentrations was added to the enzyme prior to initiation of the reaction. The reaction was performed at room temperature in a 96-well plate and was initiated with the addition of substrate. The production of fluorescent product was measured every 60 sec for 45 min with a Tecan Infinite M200 plate-reader with excitation at 355 nM and emission detected at 460 nM, with 4-Methylumbelliferone (Sigma M1381) used to produce a standard curve. The slope of product production was determined for each concentration of compound tested and plotted, using standard curve fitting algorithms for sigmoidal dose response curves. The values for a four parameter logistic curve fit of the data were determined. $K_I$ values were determined using the Cheng-Prusoff equation; the $K_m$ of O-GlcNAcase for substrate was 0.2 mM. Many compounds of the invention exhibit $K_I$ values for inhibition of O-GlcNAcase in the range 0.1 nM-10 μM. The $K_I$ values for the compounds of the examples are shown in the table below. The following table shows representative data for the compounds of the Examples as determined by the assay described herein.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of formula I:

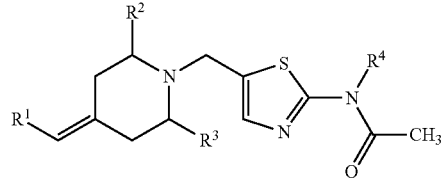

or a pharmaceutically acceptable salt thereof,
wherein:
$R^1$ is benzodioxolyl, dihydrobenzodioxinyl, oxoisoindolinyl, pyrazolyl, phenyl, pyridyl, pyrimidinyl or indolyl, wherein the benzodioxolyl, dihydrobenzodioxinyl, oxoisoindolinyl, pyrazolyl, phenyl, pyridyl, pyrimidinyl or indolyl is optionally substituted with one or more substituents selected from the group consisting of $R^{1a}$, $R^{1b}$ and $R^{1c}$;
$R^2$ is hydrogen or methyl;
$R^3$ is hydrogen or methyl;
$R^4$ is hydrogen or methyl; and
$R^{1a}$, $R^{1b}$ and $R^{1c}$ are independently halogen, $C_{1-6}$alkyl, —OH, —O—$C_{1-6}$alkyl, —O—$C_{3-6}$alkenyl, —$NO_2$, —$NH_2$, —NH($C_{1-6}$alkyl), —N($C_{1-6}$alkyl)$_2$, —C(=O)$NH_2$, —C(=O)NH($C_{1-6}$alkyl), —C(=O)N($C_{1-6}$alkyl)$_2$, —C(=O)—$C_{1-6}$alkyl, —C(=O)O—$C_{1-6}$alkyl, —OC(=O)O—$C_{1-6}$alkyl, —S(=O)$_2$$NH_2$, S(=O)$_2$N($C_{1-6}$alkyl)$_2$, or phenyl, wherein the $C_{1-6}$alkyl is optionally substituted with one or more substituents selected from the group consisting of —F, —OH, —$OCH_3$, —O($CH_2$)$_2$$OCH_3$, —C(=O)—$C_{1-6}$alkyl, —$NH_2$, —NH($C_{1-6}$alkyl), —N($C_{1-6}$alkyl)$_2$ and —NHC(=O)($C_{1-6}$alkyl), and further wherein the —O—$C_{1-6}$alkyl is optionally substituted with one or more substituents selected from the group consisting of —F, —OH, —$OCH_3$, —C(=O)—$C_{1-6}$alkyl, —$NH_2$, —NH($C_{1-6}$alkyl), —N($C_{1-6}$alkyl)$_2$, and —NHC(=O)($C_{1-6}$alkyl).

2. The compound of claim 1, or a pharmaceutically acceptable salt thereof, wherein $R^1$ is phenyl or pyridyl, each of which is optionally substituted with one or more substituents selected from the group consisting of $R^{1a}$, $R^{1b}$ and $R^{1c}$.

3. The compound of claim 1, or a pharmaceutically acceptable salt thereof, wherein:

R¹ is phenyl or pyridyl, each of which is optionally substituted with one or more substituents selected from the group consisting of $R^{1a}$ and $R^{1b}$; and $R^{1a}$ and $R^{1b}$ are independently F, $C_{1-3}$alkyl, -OH, or -O-$C_{1-3}$alkyl, wherein the $C_{1-3}$alkyl is optionally substituted with one or more substituents selected from the group consisting of F, -OH, and -OCH$_3$, and further wherein the -O-$C_{1-3}$alkyl is optionally substituted with one or more substituents selected from the group consisting of F, -OH, and -OCH$_3$.

4. The compound of claim 1, or a pharmaceutically acceptable salt thereof, wherein:

R¹ is phenyl or pyridyl, each of which is optionally substituted with one or more substituents selected from the group consisting of $R^{1a}$, $R^{1b}$ and $R^{1c}$; and $R^{1a}$, $R^{1b}$ and $R^{1c}$ are independently halogen, $C_{1-6}$alkyl, -OH, or -O-$C_{1-6}$alkyl, wherein the $C_{1-6}$alkyl is optionally substituted with one or more substituents selected from the group consisting of F, -OH, and -OCH$_3$, and further wherein the -O-$C_{1-6}$alkyl is optionally substituted with one or more substituents selected from the group consisting of F, -OH, and -OCH$_3$.

5. The compound of claim 1, or a pharmaceutically acceptable salt thereof, wherein:

R¹ is phenyl or pyridyl, each of which is optionally substituted with one or more substituents selected from the group consisting of $R^{1a}$, $R^{1b}$ and $R^{1c}$; and $R^{1a}$, $R^{1b}$ and $R^{1c}$ are independently F, $C_{1-3}$alkyl, -OH, or -O-$C_{1-3}$alkyl, wherein the $C_{1-3}$alkyl is optionally substituted with one or more substituents selected from the group consisting of F, -OH, and -OCH$_3$, and further wherein the -O-$C_{1-3}$alkyl is optionally substituted with one or more substituents selected from the group consisting of F, -OH, and -OCH$_3$.

6. The compound of claim 1, wherein the compound is of formula Ia:

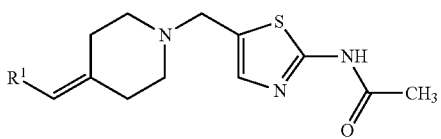

Ia or a pharmaceutically acceptable salt thereof.

7. A pharmaceutical composition comprising an inert carrier and a compound of claim 1, or a pharmaceutically acceptable salt thereof.

8. A method for inhibiting O-linked N-acetylglucosaminidase activity in a human patient, comprising administering to a human patient in need thereof a therapeutically effective amount of a compound of claim 1, or a pharmaceutically acceptable salt thereof.

9. The method of claim 8, wherein the human patient has a disease or disorder selected from the group consisting of consisting of Alzheimer's disease, Huntington's disease, Parkinson's disease, amyotrophic lateral sclerosis, progressive supranuclear palsy, glaucoma, schizophrenia, mild cognitive impairment, neuropathy, and cancer.

10. The method of claim 9, wherein the human patient has been diagnosed with a need for treatment of the disease or disorder prior to administering the compound of claim 9, or a pharmaceutically acceptable salt thereof.

11. A compound selected from the group consisting of:
N-(5-((4-(3,4-dimethoxybenzylidene)piperidin-1-yl)methyl)thiazol-2-yl)acetamide;
N-(5-((4-((6-fluoropyridin-3-yl)methylene)piperidin-1-yl)methyl)thiazol-2-yl)acetamide;
N-(5-((4-((6-hydroxypyridin-3-yl)methylene)piperidin-1-yl)methyl)thiazol-2-ypacetamide;
N-[5-({4-[(4-hydroxyphenyl)methylidene]-piperidin-1-yl)methyl)-1,3-thiazol-2-yl]acetamide;
4-((142-acetamidothiazol-5-yl)methyl)piperidin-4-ylidene)methyl)phenyltert-butyl carbonate;
N-[5-({4-[(6-aminopyridin-3-yl)methylidene]piperidin-1-yl(methyl)-1,3-thiazol-2-yl]acetamide;
N-(5-((4-(3-(hydroxymethyl)-benzylidene)piperidin-1-yl)methypthiazol-2-y)pacetamide;
N-(5-((4-((1H-pyrazol-4-yl)methylene)piperidin-1-yl)methyl)thiazol-2-yl)acetamide;
4-((1-((2-acetamidothiazol-5-yl)methyl)-piperidin-4-ylidene)methyl)benzamide;
2-(3-((142-acetamidothiazol-5-yl)methyl)-piperidin-4-ylidene)methyl)phenyl)-acetamide;
N-(5-((4-(4-(trifluoromethoxy)benzylidene)-piperidin-1-yl)methypthiazol-2-y)pacetamide;
N-(5-((4-(4-ethylbenzylidene)piperidin-1-yl)methyl)thiazol-2-yl)acetamide;
N-(5-((4-(4-methylb enzylidene)piperidin-1-yl)methyl)thiazol-2-yl)acetamide;
N-(5-((4-(4-ethoxybenzylidene)piperidin-1-yl)methyl)thiazol-2-yl)acetamide;
N-(5-((4-(pyrimidin-5-ylmethylene)piperidin-1-yl)methyl)thiazol-2-yl)acetamide;
N-[5-({4-[(2,3-dimethoxyphenyl)methylidene]piperidin-1-yl}methyl)-1,3-thiazol-2-yl]acetamide;
N-(5-((4-(4-(N,N-dimethyl sulfamoyl)benzylidene)piperidin-1-yl)methyl)thiazol-2-yl)acetamide;
N-(5-{[4-(1H-indol-5-ylmethylidene)piperidin-1-yl]methyl}-1,3-thiazol-2-ypacetamide;
N-(5-{[441,3-benzodioxol-5-ylmethylidene)piperidin-1-yl]methyl}-1,3-thiazol-2-ypacetamide;
N-(5-{[4-(2,3-dihydro-1,4-benzodioxin-6-ylmethylidene)piperidin-1-yl]methyl}-1,3-thiazol-2-yl)acetamide;
N-(5-((4-((1-oxoisoindolin-5-yl)methylene)piperidin-1-yl)methypthiazol-2-ypacetamide;
N- [5-({4-[(4-hydroxy-3-methoxyphenyl)methylidene] piperidin-1-yl }methyl)-1,3-thiazol -2-yl]acetamide;
N45-({4-[(3-hydroxy-4-methoxyphenyl)methylidene]piperidin-1-yl}methyl)-1,3-thiazol-2-yl]acetamide;
methyl4-((1-((2-acetamidothiazol-5-yl)methyl)piperidin-4-ylidene)methyl)benzoate;
N-{5-[(4-{[4-(hydroxymethyl)phenyl]-methylidene}piperidin-1-yl)methyl]-1,3-thiazol-2-yl}acetamide;
N-(5-((4-(4-(fluoromethyl)benzylidene)piperidin-1-yl)methyl)thiazol-2-yl)acetamide;
N-(5-((4-(4-(2-fluoroethyl)-benzylidene)piperidin-1-yl)methyl)thiazol-2-yl)acetamide;
N-(5-((4-(4-(2-fluoroethyl)benzylidene)-piperidin-1-yl)methyl)thiazol-2-yl)-N-methylacetamide;
4-[(1-{[2-(acetylamino)-1,3-thiazol-5-yl]methyl}piperidin-4-ylidene)methyl]benzoic acid;
4-[(1-{[2-(acetylamino)-1,3-thiazol -5-yl]methyl}piperidin-4-ylidene)methyl]-N-methylbenzamide;
4-((1-((2-acetamidothiazol-5-yl)methyl)piperidin-4-ylidene)methyl)-N,N-dimethylbenzamide;
N-[5 -({4-[(4-fluorophenyl)methylidene]piperidin-1-yl }methyl)-1,3-thiazol-2-yl]acetamide;

N-(5-{[4-(phenyl-methylidene)piperidin-1-yl]methyl}-1,
3-thiazol -2-yl)acetamide;
(S,Z)-N-(5-((4-benzylidene-2-methylpiperidin-1-yl)
methyl)thiazol-2-yl)acetamide;
(R,Z)-N-(5-((4-benzylidene-2-methylpiperidin-1-yl)
methyl)thiazol-2-yl)acetamide;
(R,E)-N-(5-((4-benzylidene-2-methylpiperidin-1-yl)
methyl)thiazol-2-yl)acetamide;
(S,E)-N-(5-((4-benzylidene-2-methylpiperidin-1-yl)
methyl)thiazol-2-yl)acetamide;
(S,Z)-N-(5-((4-(4-methoxybenzylidene)-2-methylpiperi-
din-1-yl)methyl)thiazol-2-yl)acetamide;
(R,E)-N-(5-((4-(4-methoxybenzylidene)-2-methylpiperi-
din-1-yl)methyl)thiazol-2-yl)acetamide;
(R,Z)-N-(5-((4-(4-methoxybenzylidene)-2-methylpiperi-
din-1-yl)methyl)thiazol-2-yl)acetamide;
(S,E)-N-(5-((4-(4-methoxybenzylidene)-2-methylpiperi-
din-1-yl)methyl)thiazol-2-yl)acetamide;
N-{5-[(4-{[4-(2-fluoroethoxy)phenyl]
methylidene}piperidin-1-yl)methyl]-1,3-thiazol-2-yl
}acetamide;
N-(5-((4-(3-methoxybenzylidene)piperidin-1-yl)methyl)
thiazol-2-yl)acetamide;
N-(5-((4-(3-hydroxybenzylidene)piperidin-1-yl)methyl)
thiazol-2-yl)acetamide;
N-{5-[(4-{[4-(prop-2-en-1-yloxy)phenyl]
methylidene}piperidin-1-yl)methyl]-1,3-thiazol
-2-yl}acetamide;
N-[5-({4-[(4-methoxyphenyl)methylidene]piperidin-1-yl
}methyl)-1,3-thiazol-2-yl]acetamide;
N-(5-((4-(2-methoxybenzylidene)piperidin-1-yl)methyl)
thiazol-2-yl)acetamide;
N-(5-((4-([1, 1'-biphenyl]-4-ylmethylene)piperidin-1-yl)
methyl)thiazol-2-yl)acetamide;
N-(5-((4-((6-nitropyridin-3-yl)methylene)piperidin-1-yl)
methyl)thiazol-2-yl)acetamide;
N-(5-((4-(4-(2-hydroxyethyl)benzylidene)piperidin-1-yl)
methyl)thiazol-2-yl)acetamide;
(R,Z)-N-(5-((4-((6-fluoropyridin-3-yl)methylene)-2-
methylpiperidin-1-yl)methyl)thiazol-2-yl)acetamide;
(S,Z)-N-(5-((4-((6-fluoropyridin-3-yl)methylene)-2-
methylpiperidin-1-yl)methyl)thiazol-2-yl)acetamide;
(R,E)-N-(5-((4-((6-fluoropyridin-3-yl)methylene)-2-
methylpiperidin-1-yl)methyl)thiazol-2-yl)acetamide;
and
(S,E)-N-(5-((4-((6-fluoropyridin-3-yl)methylene)-2-
methylpiperidin-1-yl)methyl)thiazol-2-yl)acetamide;
or a pharmaceutically acceptable salt thereof.
12. A compound which is:

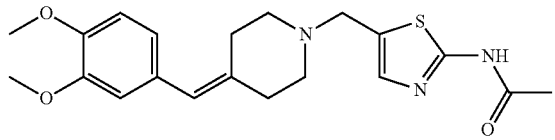 [SMILES: COc1ccc(C=C2CCN(Cc3cnc(NC(C)=O)s3)CC2)cc1OC]

or a pharmaceutically acceptable salt thereof.

13. A compound which is:

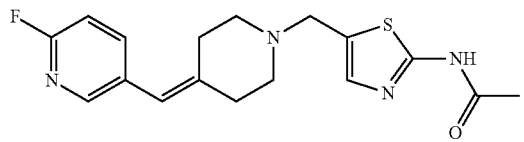 [SMILES: CC(=O)Nc1ncc(CN2CCC(=Cc3ccc(F)nc3)CC2)s1]

or a pharmaceutically acceptable salt thereof.

14. A compound which is:

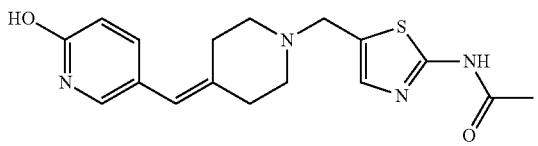 [SMILES: CC(=O)Nc1ncc(CN2CCC(=Cc3ccc(O)nc3)CC2)s1]

or a pharmaceutically acceptable salt thereof.

15. A compound which is:

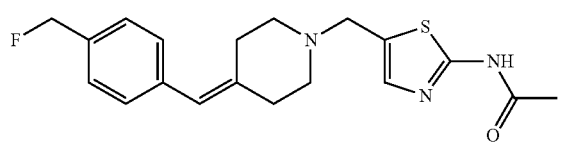 [SMILES: CC(=O)Nc1ncc(CN2CCC(=Cc3ccc(CF)cc3)CC2)s1]

or a pharmaceutically acceptable salt thereof.

16. A compound which is:

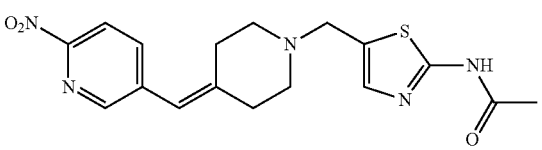 [SMILES: CC(=O)Nc1ncc(CN2CCC(=Cc3ccc([N+](=O)[O-])nc3)CC2)s1]

or a pharmaceutically acceptable salt thereof.

17. A pharmaceutical composition comprising an inert carrier and a compound of claim 11, or a pharmaceutically acceptable salt thereof.

18. A pharmaceutical composition comprising an inert carrier and a compound of claim 12, or a pharmaceutically acceptable salt thereof.

19. A pharmaceutical composition comprising an inert carrier and a compound of claim 13, or a pharmaceutically acceptable salt thereof.

20. A pharmaceutical composition comprising an inert carrier and a compound of claim 14, or a pharmaceutically acceptable salt thereof.

21. A pharmaceutical composition comprising an inert carrier and a compound of claim 15, or a pharmaceutically acceptable salt thereof.

* * * * *